US006241962B1

(12) United States Patent
Nicolini et al.

(10) Patent No.: US 6,241,962 B1
(45) Date of Patent: Jun. 5, 2001

(54) RADIOPHARMACEUTICAL COMPOSITIONS AND MATRICES AND USES THEREOF

(75) Inventors: Jorge Osvaldo Nicolini; Ricardo Julio Ughetti, both of Pcia. Buenos Aires (AR)

(73) Assignee: Dupont Pharmaceuticals Company, Wilmington, DE (US)

( * ) Notice: Subject to any disclaimer, the term of this patent is extended or adjusted under 35 U.S.C. 154(b) by 0 days.

(21) Appl. No.: 08/869,460

(22) Filed: Jun. 5, 1997

Related U.S. Application Data

(63) Continuation-in-part of application No. 08/669,169, filed on Jun. 24, 1996, now abandoned.

(51) Int. Cl.$^7$ .......................... A61K 51/00; A61M 36/14
(52) U.S. Cl. ..................... 424/1.61; 424/1.11; 424/9.1
(58) Field of Search .................... 424/1.11, 1.61, 424/1.77, 9.1; 206/223, 569, 570; 534/7, 10–16

(56) References Cited

U.S. PATENT DOCUMENTS

| 4,323,055 | 4/1982 | Kubiatowicz | 128/1.2 |
|---|---|---|---|
| 4,706,652 | 11/1987 | Horowitz | 128/1.2 |
| 4,815,449 | 3/1989 | Horowitz | 600/7 |
| 4,935,222 | * 6/1990 | Deutsch et al. | 424/1.11 |

(List continued on next page.)

OTHER PUBLICATIONS

Andrews, J. et al., "Hepatic Radioembolization with Yttrium–90 Containing Glass Microspheres: Preliminary Results and Clinical Follow–Up", *J. Nucl. Med.*, 1994, 35, 1637–1644.
Anghileri, L. J., "In Vivo Distribution of Radioactive Chromic Phosphate: Influence of the Particle Size and Route of Injection", *Int. J. Applied Radiation and Isotopes* 1965, 16, 623–630.
Bell, "Composition of Strong Phosphoric Acids", *Industrial and Engineering Chem.*, 1948, 40, 1464–1467.
Blasko, J. et al., "External Beam Irradiation with Palladium–103 Implantation for Prostate Carcinoma", Proceedings of the 36th Annual ASTRO Meeting, Abstract No. 114, p. 219.
Blasko, J. et al., "Transperineal Percutaneous Iodine–125 Implantation for Prostatic Carcinoma Using Transrectal ultrasound and Template Guidance", *Endocurie, Hypertherm, Oncol.*, 1987, 3, 131–139.
Blend, M.J. et al., "Radiation Splenectomy Utilizing Intra–Arterial P–32 Chronic Phosphate: A Preliminary Study", *J. Nuclear Medicine Proceedings of the 36th Annual Meeting*, 1989, 30(5), Abstract No. 655, p. 884.
Buell, Udalrich, "Scientific Highlights of the European Nuclear Medicine Congress 1985", *J. Nuclear Medicine* 1985, 26(11), 1227.

"Consensus Conference: The Management of Clinically Localized Prostate Cancer", *J. Am. Med. Assoc.*, 1987, 258 (19), 2727–2730.
Crusinberry, R. et al., "Percutaneous Transperineal Placement of Gold 198 Seeds for Treatment of Carcinoma of the Prostate", *The Prostate*, 1987, 11, 59–67.
Freeman, M. et al., "Studies with Encapsulated $^{125}$I Sources. II. Determination of the Relative Biological Effectiveness Using Cultured Mammalian Cells", *Int. J. Radiation Oncology Biol. Phys.* 1982, 8, 1355–1361.
Girado, M. and Lanari, "Nuevo Compuesto (Pirocarbotrat) P32 en Braquiterapia del Sistema Nervioso Central", *Boletín de la Asociacín Argentina de Neurocirugía*, No. 39, 1992, p. 82.
Gullino et al., "N–Nitrosomethylurea as Mammary Gland Carcinogen in Rats", *Natl. Cancer Inst.*, 1975, 54, 401–404.
Hatfield, S., "PSA Blood Test Will It Dictate When Radiation Therapy Begins?", *ADVANCE for Radiologic Science Professionals*, 1995, 20.
Jaffe, H., "Interstitial use of Radioactive Colloidal Chromic Phosphate in Therapy", Chapter 40 in *Radioscopes in Medicine*, U.S. Atomic Energy Commission, Sep. 1953 (pub.).
Jaroff, L., "The Man's Cancer", *Time*, 1996, 58–65.
Kaye, K.W. et al., "Improved Technique for Prostate Seed Implantation; Combined Ultrasound and Fluoroscopic Guidance", *Endourology* 1992, 6 (1), 61–66.
Kaye, K. et al., "Detailed Preliminary Analysis of $^{125}$Iodine Implantation for Localized Prostate Cancer Using Percutaneous Approach", *J. Urology*, 1995, 153, 1020–1025.
Kallus, M.A. et al., "Treatment of Cystic Brain Tumor: Distribution of 32–P–Chromic Phosphate Colloid (32–P–CPC) in Cyst Fluid", *J. Nuclear Medicine, Proceedings of the 36th Annual Meeting*, May 1989, 30 (5), Abstract No. 436, pp. 833–834.
Levine, G. et al., "Phosphorus–32 Therapy of Cystic Brain Tumors", *J. Nuclear Med.*, 1986, 27 (9), 1503–1504.
Loening, S.A. and Rosenberg, "Percutaneous Placement of Radioactive Gold Seeds in Localized Prostatic Carcinoma", *Urology*, 1967, 29 (3), 250–252.
McGuire, E.L. et al., "Dosimetry for Cystic–Type Tumors", *J. Nuclear Med.*, 1986, 27 (9), 1501–1503.
"Phosphocol$^{TM}$ P 32 Chromic Phosphate P 32 Suspension", Product Information published by Mallinckrodt Medical, 9/92.

(List continued on next page.)

*Primary Examiner*—Dameron L. Jones
(74) *Attorney, Agent, or Firm*—Rothwell, Figg, Ernst & Manbeck

(57) ABSTRACT

Novel radiopharmaceutical compositions comprising, in combination with a pharmaceutically acceptable carrier, a radioactive salt of pyrophosphoric acid. Also provided are novel radiopharmaceutical compositions comprising, in combination with one or more polymeric resins, a radioactive salt of pyrophosphoric acid. The compositions and matrices are suitable, inter alia, for use in treatment methods involving brachytherapy.

78 Claims, 25 Drawing Sheets

U.S. PATENT DOCUMENTS

| | | | |
|---|---|---|---|
| 5,163,896 | 11/1992 | Suthanthiran et al. | 600/8 |
| 5,282,781 | 2/1994 | Liprie | 600/3 |
| 5,368,840 | 11/1994 | Unger | 424/9 |
| 5,432,168 | 7/1995 | Brandes | 514/90 |

OTHER PUBLICATIONS

Pasteau, O. et al., "Maladies Des Voies Urinaires: Traitement Du Cancer De La Prostate Par Le Radium", *Rev. Malad. Nutr.*, 1911, 363–384.

Porter, A.T. et al., "Brachytherapy for Prostate Cancer", *CA Cancer J. Clin.*, 1995, 45 (3), 165–178.

Rivera et al., "Unduction of Mammary Tumors in Rat by Intraperitoneal Injection of NMU: Histopathology and Estral Cycle Influence", *Cancer Lett.*, 1994, 86, 223–228.

Schellhammer, P. et al., "[125]Iodine Implantation for Carcinoma of the Prostate: 5–Year Survival Free of Disease and Incidence of Local Failure", *J. Urology*, 1985, 134, 1140–1145.

Sprenglemeyer, J.T. et al., "Phosphorus–32–Colloidal Chromic Phosphate: Treatment of Choice for Malignant Percardial Effusion", *J. Nuclear Med.*, 1990, 31 (12), 2034–2036.

Taasan, V. et al., "Phosphorus–32 Therapy of Cystic Grade IV Astrocytomas; Technique and Preliminary Application", *J. Nucl. Med.*, 1985, 26 (11), 1335–1338.

Van Nostrand, D. et al., "Therapeutic Uses of $^{32}$P", *Nuclear Medicine Annual*, Raven Press, New York, 1985, 285–344.

Wallner, K. et al., "Short–Term Freedom from Disease Progression After I–125 Prostate Implantation", *Int. J. Radiation Oncology Biol. Phys.*, 1994, 30 (2), 405–409.

Wu, J. And Anscher, "The Efficacy of Post–Prostatectomy Radiotheraphy in Patients with a Rising Prostate Specific Antigen", Proceedings of the 36th Annual ASTRO Meeting, Abstract No. 115, p. 219.

Zielinski, Fl. And Kasprzyk, "Synthesis and Quality Control Testing of $^{32}$P Labeled Ion Exchange Resin Microspheres for Radiation Therapy of Hepatic Neoplasms", *Int. J. Appl. Radiat. Isot.*, 1983, pp. 34 (9), 1343–1350.

Zubillaga, M.B. et al., "Great Particles [$^{32}$P] Chromic Phosphate for Treatment of Solid Tumors", *Acta Physiologica Pharmacologica et Therapeutica Latinoamericana*, 1996, 46 (2), 103–110.

Schweitzer, G.K. et al., "Low–Concentration Chemistry. VII. The Role of Absorption in Radiocolloid Formation", *J. Am. Chem. Soc.*, 1954, 76, 941–944 (Abstract only).

Graul. E.H., "Radiocolloid Therapy", *Medica Mundi*, 1958, 4, 37–56 Abstract only).

Levin, V.I. et al., "Physico–Chemical Properties of a Radiotherapeutic Preparation Containing $P^{32}$", *Med. Radiol.*, 1960, 5 (4), 53–55 (Abstract only).

Bellion, B. et al., "Phosphorus–32 Labeled Colloid", *Minerva Nucl.*, 1963, 7 (6), 237–243 (Abstract only).

Angoso, M. "Colloidal Zirconyl Phosphates Containing $^{32}$P", *Anales Real Soc. Espan. Fis. Quim.*, 1964, 60 (5), 391–396 (Abstract Only).

Angoso, M., "Colloidal Chromium Phosphates with $^{32}$P", *Anales Real Soc. Espan. Fis. Quim.*, 1964, 60 (5), 381–90 (Abstract only).

Tarasov, N.F., "Administration of Radioactive Colloidal Solutions of $^{198}$Au, $^{32}$P, and $^{111}$Ag into the Lymph Vessels", *Med. Radiol.* 1965, 10 (5), 61–66 (Abstract only).

Kurebart, H. And Radicella, "A New $^{32}$P–Labeled Colloid for Medical Use", *Intern J. Appl. Radiation Isotopes* 1965, 16 (12), 749–751 (Abstract only).

Priestly, J.B. and Beyer, "Guided Brachytherapy for Treatment of Confined Prostate Cancer", *Urology*, 1992, 40 (1), 27–32.

Zubillaga et al., "Use of Colloids of Chromic [$^{33}$P] Phosphate in Treatment of Solid Tumors", *Nuclear Med. & Biol.*, 1996, 23, 907–910.

PCT International Search Report dated Oct. 30, 1997, 1 page.

Lerch et al., Proc. Int–Conf. Methods Prep. Stor. Label. Compounds, $2^{nd}$ Meeting Date 1966, pp. 1145–1154.

\* cited by examiner

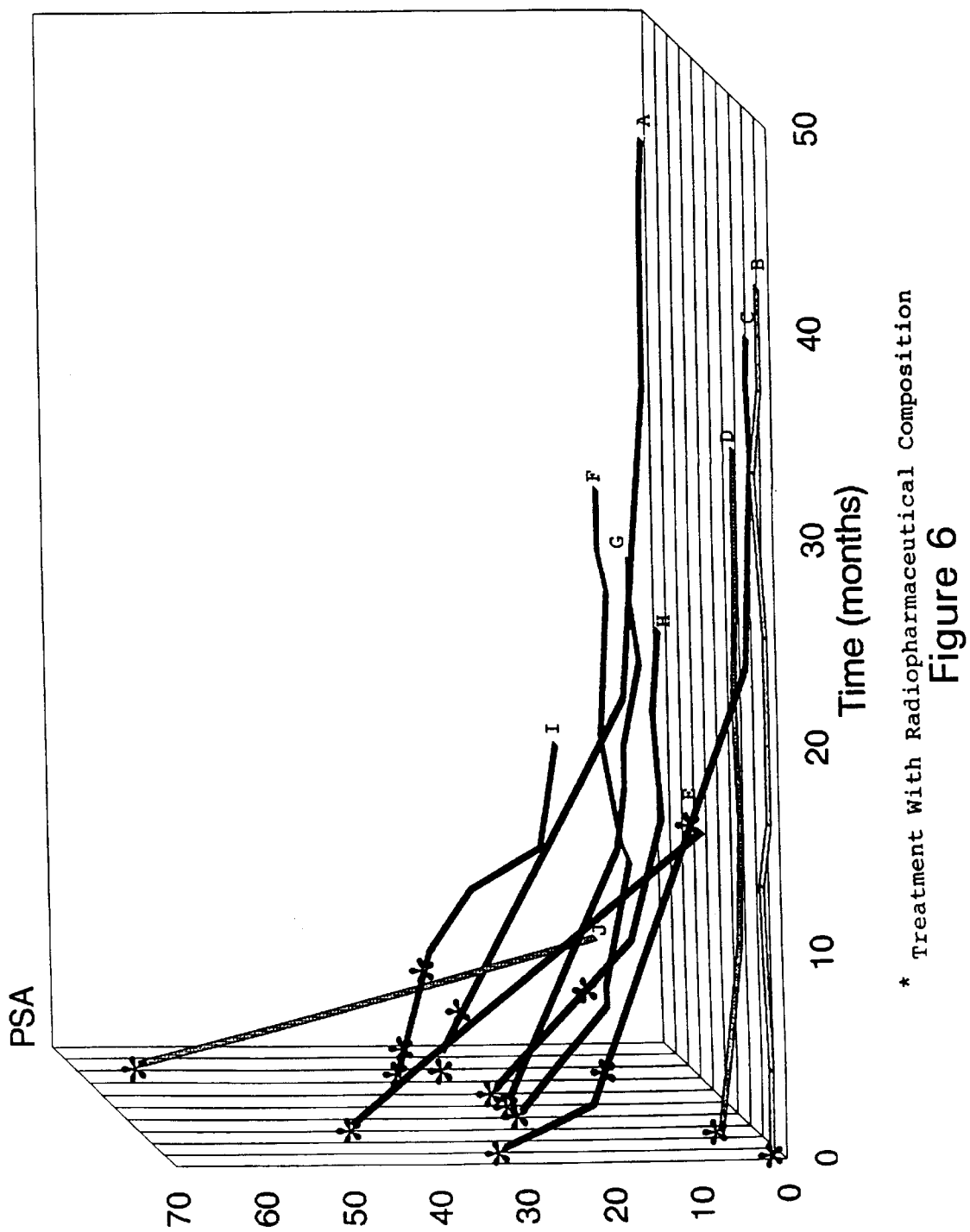

RADIOPHARMACEUTICAL COMPOSITIONS AND MATRICES AND USES THEREOF

CROSS-REFERENCE TO RELATED APPLICATION

This application is a continuation-in-part of copending U.S. application Ser. No. 08/669,169, filed Jun. 24, 1996, now abandoned the disclosures of which are hereby incorporated herein by reference, in their entirety.

FIELD OF THE INVENTION

The present invention relates to novel radiopharmaceutical compositions and matrices and the use thereof. More particularly, the present invention relates to novel radiopharmaceutical compositions and matrices for use in radiotherapy.

BACKGROUND OF THE INVENTION

It has been predicted that one-third of all individuals in the United States may develop cancer. Cancer remains second only to cardiovascular disease as a cause of death in this country. More than 20% of Americans die from cancer, and this figure has been rising steadily as the population ages and deaths from heart disease decline. In the U.S., malignancy accounted for 526,000 deaths in 1992. Breast cancer is the most common form of malignancy in women (and is considered non-preventable), whereas prostate cancer is the most common form of malignancy in men in the U.S.

In 1995, there were approximately 230,000 newly diagnosed cases of prostate cancer and more than 44,000 deaths from prostate cancer in the U.S. alone. The disease is rare before age 50, and its incidence increases with age. The frequency of prostate cancer varies in different parts of the world. For example, the U.S. has 14 deaths per 100,000 men per year compared with 22 for Sweden and 2 for Japan. However, Japanese immigrants to the U.S. develop prostatic cancer at a rate similar to that of other men in this country. This suggests that an environmental factor may be the principal cause for population differences.

Despite these statistics, the appropriate treatment for cancer of the prostate remains controversial. Methods of treatment have included radiotherapy, such as external beam radiotherapy, and prostatectomy. Of these, radiotherapies were developed in an effort to avoid the undesirable side effects, including impotence and occasional incontinence, which are often associated with prostatectomy. Nevertheless, radiotherapies, and especially external beam therapies, may also produce undesirable side effects. Specifically, chronic complications after full courses of external beam radiation often occur, including impotence, chronic proctitis and rectal stricture, fistula or bleeding. In addition, it is not clear whether external beam radiation actually eradicates prostate cancer, because many patients in whom progression of the tumor is slowed or halted have persistent tumor on rebiopsy. The biologic potential of these persistent tumors is not clear. Also, once external beam radiation has been initiated, other methods of treatment, such as those involving surgery, are generally prohibited thereafter.

An alternative to external beam radiation treatment is brachytherapy. Brachytherapy generally refers to radiotherapy in which the source of radiation is located proximate the area of the body which is being treated. Brachytherapy typically involves the implantation of a radiation source, commonly referred to as "seeds", directly into a tumor. These seeds may consist of radioisotopes or radiolabelled compounds. Brachytherapy offers the appealing concept of delivering a high dose of radiation to a confined area with relative sparing of adjacent normal tissue. Brachytherapy is one of the oldest techniques of radiotherapy for prostate cancer. In 1911, the first report on brachytherapy treatment for prostate cancer, which involved the insertion of radium into the prostatic urethra via catheter, was published. O. Pasteau et al., *Rev. Malad. Nutr.*, pp. 363–367 (1911). Over the past 10 years, improvements in methods for brachytherapy have been stimulated by advances in technology, including innovative afterloading techniques, treatment planning by computer-based dosimetry analysis, and modem imaging modalities, as well as an improved understanding of the radiobiology associated with different dose rates of radiation. As a result, brachytherapy has been used successfully in the treatment of many cancers other than prostate cancer, including carcinomas of the cervix, breast, endometrium, head and neck.

The prostate is located adjacent to the critical structures of the bladder, urethra and rectum, and is therefore well-suited to confined radiation doses created by the implantation of radioactive seeds. Brachytherapy can deliver more radiation to the prostate with less dosages to the surrounding normal tissue than conventional external-beam radiation therapy. This higher intraprostatic dose should theoretically result in more effective tumor treatment, with fewer complications. However, the use of brachytherapy for carcinoma of the prostate is controversial because of the mixed results which have been reported and because of the availability of other treatment methods.

Methods of implantation in brachytherapy may involve temporary implantation, where the radiation source is left in the patient for a defined period of time and thereafter removed, or permanent implantation, where the radiation source is implanted permanently into the patient and is permitted to decay over a period of time into an inert state. Included among the radioisotopes which have been employed in brachytherapy include iodine 125 ($^{125}$I), gold 198 ($^{198}$Au), palladium 103 ($^{103}$Pd), ytterbium 169 ($^{169}$Yb) and iridium 192 ($^{192}$Ir).

Radiation sources, such as radioisotopes, are characterized by the kind and energy of particles and/or photons which they emit, as well as their half-life. Radioisotopes, such as $^{192}$Ir and $^{198}$Au, which are typically encapsulated, for example, in titanium, generally deliver only photons to the patient which may penetrate further into tissue. The position of these sources is generally less critical to the achievement of a homogenous dose. However, this greater depth of radiation penetration may result in a greater exposure of surrounding normal tissue to radiation. The radiation of low to moderate energy sources, such as $^{125}$I, $^{103}$Pd and $^{169}$Yb, may deliver a more confined dose of radiation, but should be placed in vivo with great precision to avoid areas of underdosage (cold spots) in the cancer due to the limited penetration of the low-energy radiation, as well as the exposure to radiation of nearby healthy tissue, such as the urethra and rectum. Thus, the delivery of an effective dosage of radiation with radiation sources that are currently available can be difficult.

Phosphorous 32 ($^{32}$P) has also been used in brachytherapy. For example, radiotherapy of cystic brain tumors with $^{32}$P is reported in V. Tassan et al., *J Nucl. Med.*, Vol. 26(11), pp. 1335–1338 (1985). $^{32}$P can be a desirable isotope for brachytherapy since it is a pure β⁻ emitter. The radiation emitted from $^{32}$P has a maximum penetration in water of 7 to 8 mm and a mean penetration in water of 1 to 4 mm. D.

Van Nostrand et al., *Nuclear Medicine Annual*, Raven Press, New York (1985). $^{32}P$ is generally incorporated in radiopharmaceuticals as the phosphate salt, particularly as chromic phosphate ($Cr^{32}PO_4$). See, e.g., J. T. Sprengelmeyer et al., *The Journal of Nuclear Medicine*, Vol. 31(12), pp. 2034–2036 (1990). However, such phosphate salts may be soluble in blood plasma and, accordingly, may be distributed throughout the body by the circulatory system. As a result, the phosphate salts may circulate from the site of implantation to other, non-cancerous regions of the body, including bone marrow and liver. L. J. Anghileri, *International Journal of Applied Radiation and Isotopes*, Vol. 16, pp. 623–630 (1965). This is highly undesirable in that it may result in the exposure of normal tissues to potentially harmful radiation. In addition, this solubility in blood plasma may result in a reduction in the concentration of phosphate salt at the site of implantation and, accordingly, a reduction in the amount of radioactivity to which the tumor is exposed. This may result in inefficient or incomplete treatment and continued growth of the tumor.

Accordingly, new and/or better radiopharmaceuticals, as well as methods for the treatment of disease are needed. The present invention is directed to these, as well as other, important ends.

SUMMARY OF THE INVENTION

The present invention is directed, in part, to radiopharmaceuticals. Specifically, in one embodiment, there is provided a radiopharmaceutical composition which comprises a radioactive salt of the Formula I $$M^{z+}H_xP_2O_7 \qquad (I)$$

wherein:

M is a metal ion;

x is an integer from 0 to 3; and z is an integer from 1 to 4;

with the provisos that the sum of x and z is equal to 4, and at least one of M, H, P and O comprises a radioisotope; and a pharmaceutically acceptable carrier.

Another embodiment of the invention relates to a radiopharmaceutical composition comprising a radioactive salt of pyrophosphoric acid and a pharmaceutically acceptable carrier.

Yet another embodiment of the invention relates to a radioactive salt of pyrophosphoric acid.

Still another embodiment of the invention relates to a solid radiopharmaceutical matrix comprising a biocompatible sleeve which substantially surrounds a radiopharmaceutical composition comprising a radioactive salt of pyrophosphoric acid and one or more polymeric resins.

Another embodiment of the invention relates to a process for the preparation of a radiopharmaceutical composition. The process comprises providing a radioactive salt of pyrophosphoric acid, and combining the salt with a pharmaceutically acceptable carrier.

Still another embodiment of the invention relates to a process for the preparation of a solid radiopharmaceutical matrix. The process comprises providing a biocompatible sleeve which substantially surrounds a mixture of a radioactive salt of pyrophosphoric acid and a curable polymeric resin, and curing said resin.

Yet another embodiment of the invention relates to a radiopharmaceutical kit comprising a radioactive salt of pyrophosphoric acid.

Highly desirable and unexpected benefits are achieved with embodiments of the present invention. Specifically, the novel radioactive salts described herein, and compositions and matrices containing them, are highly useful in methods for the treatment of diseases, such as cancer, especially treatment methods involving brachytherapy. The radioactive salts and radiopharmaceutical compositions and matrices of the present invention are generally substantially insoluble in aqueous media, including blood and other bodily fluids. Accordingly, the present radioactive materials generally do not solubilize and circulate in the blood to a location in the body which is different from the site of implantation. Thus, the present invention may avoid the highly undesirable exposure of normal tissues in the body to potentially harmful radiation, which may occur, for example, with radiopharmaceuticals of the prior art. In addition, since the implanted radiopharmaceutical compositions and/or matrices substantially remain at the site of implantation, the cancer may be treated with desirable and controllable dosages of radiation.

These and other aspects of the invention will become more apparent from the present specification and claims.

BRIEF DESCRIPTION OF THE DRAWINGS

FIG. 6 is a graphical representation of pharmacological test studies of radiopharmaceuticals according to an embodiment of the present invention.

DETAILED DESCRIPTION OF THE INVENTION

Figure 1:
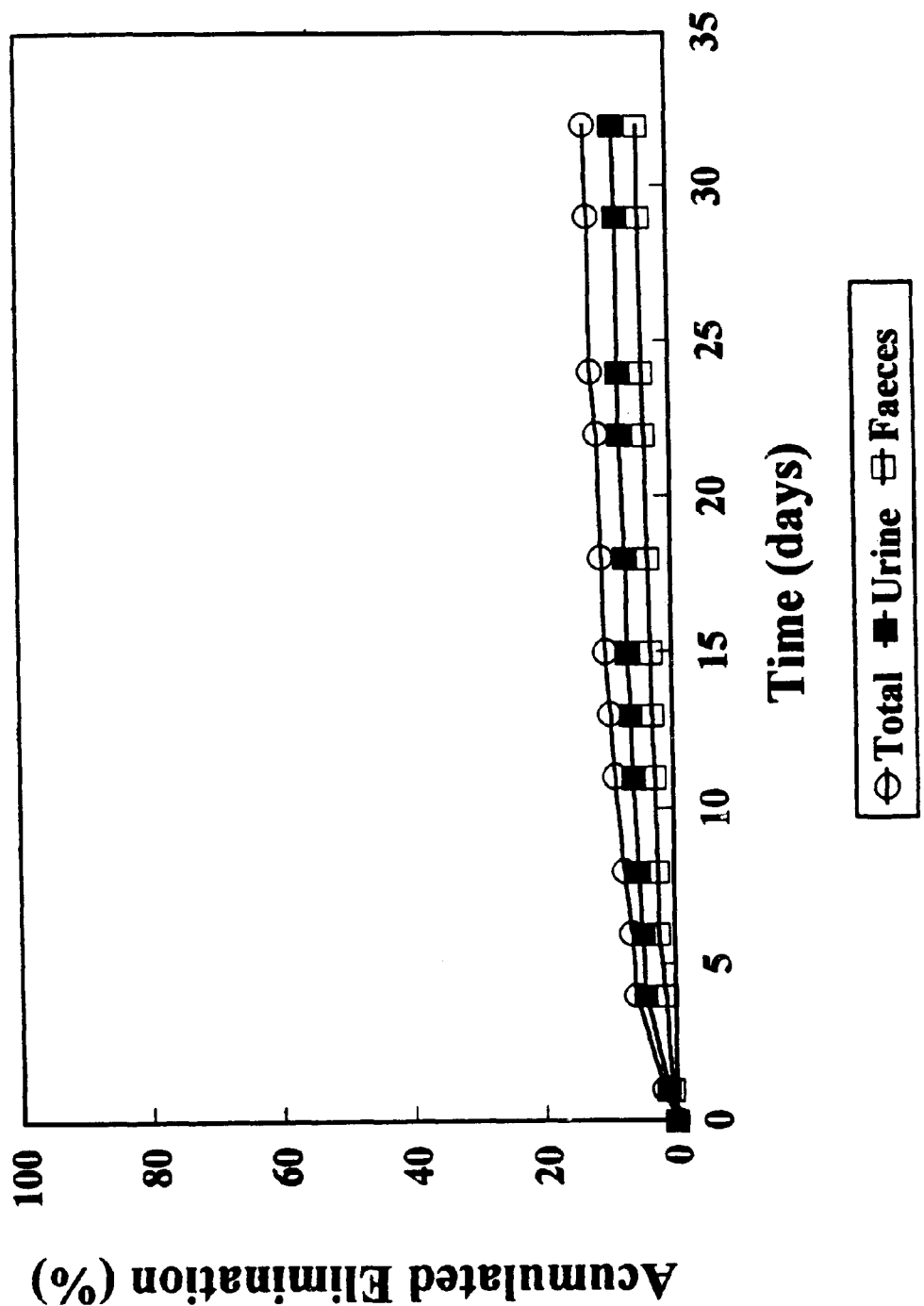
FIG. 1 is a graphical representation of studies of the biological elimination of radiopharmaceuticals according to an embodiment of the present invention.

The present invention is directed, in part, to radiopharmaceutical compositions. Broadly speaking, the present radiopharmaceutical compositions comprise a radioactive salt and a pharmaceutically acceptable carrier. As known to those skilled in the art, salts are compounds which may be produced from the reaction between acids and bases, and generally comprise a positive ion (cation) and a negative ion (anion). The positive and negative ions can each comprise a single element, or a combination of two or more elements. Thus, in the context of the present invention, at least one of the elements in the positive or negative ions of the radioactive salts is a radioisotope.

As noted above, radioactive salts which are known and which may be used in brachytherapy include salts of phosphoric acid, such as, for example, chromium (III) phosphate ($Cr^{32}PO_4$). However, salts of phosphoric acid which have been known heretofore, as in the case of $Cr^{32}PO_4$, also generally possess highly undesirable properties including, for example, undesired solubility in blood. It has been unexpectedly and surprisingly discovered that radioactive compounds which may be derived from pyrophosphoric acid ($H_4P_2O_7$) may lack the undesired solubility in blood that is generally characteristic of salts of phosphoric acid. Thus, in accordance with the present invention, the radioactive salts preferably comprise salts of pyrophosphoric acid. In preferred form, the radioactive salts are represented by the Formula I $$M^{z+}H_xP_2O_7 \quad (I)$$

wherein:

M is a metal ion;

x is an integer from 0 to 3; and z is an integer from 1 to 4;

with the provisos that the sum of x and z is equal to 4, and at least one of M, H, P and O comprises a radioisotope (that is, the compound of Formula (I) comprises at least one radioisotope).

Preferably, M is selected from the group consisting of indium (In), calcium (Ca), strontium (Sr) and transition metals. Preferably, M is a transition metal. Preferred among the transition metals are those selected from the group consisting of chromium (Cr), yttrium (Y), holmium (Ho), samarium (Sm), iron (Fe), gold (Au), silver (Ag), cerium (Ce) and mixtures thereof, with chromium being more preferred. It is contemplated that various of the oxidation states of the metal ions listed above are included within the definition of M. Thus, when M is, for example, chromium, the chromium ion can be present as $Cr^{2+}$, $Cr^{3+}$ or $Cr^{4+}$. In particularly preferred embodiments, M is chromium, x is 0 or 1 and z is 3 or 4. Thus, for example, when M is chromium, x is 0 and z is 3, the compound of Formula (I) may be depicted, for example, as $Cr_4(P_2O_7)_3$.

The radioactivity of the salts described herein, including the preferred salts of Formula (I), arises from the presence of at least one radioisotope. Thus, in embodiments which involve radioactive salts of the compound of Formula (I), at least one of M, H, P or O comprises a radioisotope. Preferably, at least one of M, P or O comprises a radioisotope. More preferably, at least one of M or P comprises a radioisotope.

As known to one of ordinary skill in the art, different radioisotopes may differ markedly in their properties, including, for example, the particular type or types of energy emitted therefrom, the mean and maximum energies of the emitted particles, the mean and maximum depths of penetration of the emitted particles in water or in other media, including, for example, soft biological tissue, and the like. Thus, the particular radioisotope incorporated in the salts described herein may affect the radioactive properties of the resulting radioactive salt. A wide variety of radioisotopes may be included in the present radioactive salts and may be selected, as desired, based on the properties which are sought to be present in the radioactive salt.

In accordance with a preferred embodiment of the invention, the radioactive salts comprise a radioisotope which is an emitter of β⁻ particles, with radioactive salts which comprise radioisotopes that substantially emit β⁻ particles being more preferred. "Substantially", as used herein, refers to radioisotopes wherein the emitted particles are at least about 50%, preferably at least about 75%, and more preferably at least about 90%, β⁻ particles. Particularly preferred are radioisotopes wherein greater than about 90% of the particles emitted are β⁻ particles. Also preferred are radioactive salts which comprise radioisotopes having a mean energy of less than about 2 MeV, such as radioisotopes having a mean energy which ranges from about 0.2 to about 1.8 MeV, and all combinations and subcombinations of ranges therein. More preferably, the radioactive salts comprise radioisotopes having a mean energy of from about 0.3 to about 1.6 MeV, with radioisotopes having mean energies of from about 0.4 to about 1.4 MeV being even more preferred. Still more preferably, the radioactive salts comprise radioisotopes having a mean energy of from about 0.5 to about 1.2 MeV, with radioisotopes having mean energies of from about 0.6 to about 1 MeV being even more preferred. Particularly preferred are radioactive salts which comprise a radioisotope having a mean energy of from about 0.7 to about 0.8 MeV.

Also in preferred embodiments of the invention, the radioactive salts comprise a radioisotope which has a maximum energy of less than about 5 MeV, such as radioisotopes having a maximum energy which ranges from about 0.2 to about 4.5 MeV, and all combinations and subcombinations of ranges therein. More preferably, the radioactive salts comprise radioisotopes having a maximum energy of from about 0.4 to about 4 MeV, with radioisotopes having maximum energies of from about 0.6 to about 3.5 MeV being still more preferred. Still more preferably, the radioactive salts comprise radioisotopes having a maximum energy of from about 0.8 to about 3 MeV, with radioisotopes having maximum energies of from about 1 to about 2.5 MeV being even more preferred. Yet more preferred are radioactive salts which comprise radioisotopes having a maximum energy of from about 1.2 to about 2 MeV, with radioisotopes having maximum energies of from about 1.4 to less than about 2 MeV being still more preferred. Particularly preferred are radioactive salts which comprise a radioisotope having a maximum energy of from about 1.6 to about 1.8 MeV.

As noted above, certain radioisotopes of phosphorous may possess properties which make them especially useful in treatments involving brachytherapy. For example, the radioisotope $^{32}P$ is a pure β⁻ emitter and the particles emitted therefrom have a maximum penetration in water of from 7 to 8 mm and a mean penetration in water of from 1 to 4 mm. Thus, radioactive materials which comprise radioisotopes of phosphorous, and especially $^{32}P$, may be advantageously used to irradiate cancerous tissue in vivo while minimizing exposure and potential damage to normal tissues proximate the cancerous tissue. However, as noted above, radioactive materials known heretofore which comprise radioisotopes of phosphorous have also possessed highly undesirable properties, including, for example, undesired solubility in blood. It is believed that, due to this solubility, these prior art radioactive materials may have a tendency to be distributed in the bloodstream to, and result in the exposure of, non-cancerous regions in the body to potentially harmful radiation. Also, due to this solubilization in the blood, the concentration of the prior art radioactive materials at the site of implantation may be reduced. This may result in a reduction in the amount of radioactivity to which the cancerous tissue is exposed.

To avoid exposure of normal tissue to radioactivity and/or a reduction in the concentration of radioactive materials at the site of implantation, it has generally been necessary to refrain from using radioactive materials which have solubility in blood, including the prior art radioactive materials which contain radioisotopes of phosphorous. This is undesirable since, as noted above, radioisotopes of phosphorous, and especially $^{32}P$, may possess highly desirable properties which make them well-suited for brachytherapy. It has now been surprisingly and unexpectedly found that radioactive salts of pyrophosphoric acid, which represent a preferred embodiment of the invention, may possess especially advantageous properties when they comprise a radioisotope of phosphorous. Not only are such salts desirably substantially insoluble in aqueous media, including blood, they may also possess desirable mean and maximum penetration depths in water and biological tissue, as well as desirable half-lives. Thus, distribution in the blood of salts which contain radioisotopes of phosphorous may be substantially avoided. This may prevent exposure of non-cancerous regions in the body to potentially harmful radiation, as well as the reduction in the quantity of radiation to which the cancerous tissue is exposed.

Accordingly, a preferred embodiment of the invention is represented by the compounds of Formula (I) above in which phosphorous (P) comprises a radioisotope.

As known to one of ordinary skill in the art, phosphorous can exist as a stable isotope ($^{31}$P) and or as a variety of radioisotopes, including, for example, $^{28}$P, $^{29}$P, $^{30}$P, $^{32}$P, $^{33}$P and $^{34}$P. It is contemplated that the phosphorous atom of the pyrophosphate moiety may comprise any one, or combinations of two or more of these radioisotopes of phosphorous. Preferably, the phosphorous atom of the pyrophosphate moiety comprises $^{32}$P.

Also as known to one of ordinary skill in the art, the other elements in the compounds of Formula (I), including hydrogen ($^1$H) and oxygen ($^{16}$O), and those represented by M, including, for example, indium ($^{115}$In), chromium ($^{52}$Cr) and yttrium ($^{89}$Y), may exist as a variety of isotopes and radioisotopes. Thus, in embodiments in which M, H or O comprises an isotope or a radioisotope, M may be, for example, a stable or a radioactive isotope of indium, including $^{106}$In, $^{107}$In, $^{108}$In, $^{109}$In, $^{110}$In, $^{111}$In, $^{112}$In, $^{113}$In, $^{114}$In, $^{116}$In, $^{117}$In, $^{118}$In, $^{119}$In, $^{120}$In, $^{121}$In, $^{122}$In, $^{123}$In or $^{124}$In; chromium including $^{48}$Cr, $^{49}$Cr, $^{50}$Cr, $^{51}$Cr, $^{53}$Cr, $^{54}$Cr, $^{55}$Cr or $^{56}$Cr; or yttrium, including $^{82}$Y, $^{83}$Y, $^{84}$Y, $^{85}$Y, $^{86}$Y, $^{87}$Y, $^{88}$Y, $^{89}$Y, $^{90}$Y, $^{91}$Y, $^{92}$Y, $^{93}$Y, $^{94}$Y, $^{95}$Y or $^{96}$Y; hydrogen can be $^2$H or $^3$H; and oxygen can be $^{13}$O, $^{14}$O, $^{15}$O, $^{17}$O, $^{18}$O, $^{19}$O or $^{20}$O.

Radioactive salts of pyrophosphoric acid may be prepared utilizing methods which would be readily apparent to one skilled in the art, once armed with the present disclosure. Generally speaking, radioactive salts of pyrophosphoric acid may be obtained by dehydration of radiolabelled orthophosphoric acid ($H_3PO_4$) or a salt thereof, such as sodium orthophosphate radiolabelled with $^{32}$P. Radiolabelled orthophosphoric acid and salts thereof are commercially available from NEN (Boston, Mass.) and ICN Biomedicals, Inc. (Irvine, Calif.). Dehydration of the orthophosphate to the corresponding pyrophosphate may be achieved using methods which are well known to those skilled in the art, including, for example, heating to elevated temperatures, as described in Bell, *Ind Eng Chem.*, Vol. 40, p. 1464 (1948).

The radioactive salts of the present invention may be especially useful in the treatment of cancer in a patient using brachytherapy, although other patient treatments are also within the scope of the present invention. "Patient", as used herein, refers to animals, including mammals, and preferably humans. In embodiments which involve salts of pyrophosphoric acid containing radiolabelled phosphorous, and especially $^{32}$P, the implantation of the radioactive salts in a tumor in vivo may provide desirable exposure of the tumor to radiation while minimizing the exposure to radiation of nearby, normal tissue. It is contemplated that a wide variety of cancers, especially solid tumor cancers, may be treated using the radioactive salts of the present invention. Examples of such solid tumor cancers include, for example, cancers of the head, such as brain cancer, and cancers of the neck, endometrium, liver, breast, ovaries, cervix and prostate. Embodiments of the invention which involve radioactive salts of pyrophosphoric acid, including compounds of Formula (I), may be particularly suitable for use in the treatment of cancer of the prostate.

The radioactive salts of the present invention may be administered to the patient in a variety of forms, depending on the particular route of administration, the particular salt and/or isotope involved, the particular cancer being treated, and the like. In the case of brachytherapy, the radioactive salts may be administered using techniques which are well known to those skilled in the art, including, for example, surgical implantation. In the case of the administration of radioactive salts in the form, for example, of an aqueous composition or suspension (discussed more fully hereafter), the aqueous composition or suspension may be administered by being injected at the desired site. In addition, the radioactive salts of the present invention may be administered in the form of a radiopharmaceutical matrix (discussed more fully hereafter), also by injection or surgical implantation at the desired site. The particular technique employed for administering the matrix may depend, for example, on the shape and dimensions of the involved matrix. Generally speaking, the introduction of the radioactive salts of the present invention for the treatment of prostate cancer may involve retropubic or transperineal techniques. See A. T. Porter et al., *CA Cancer J. Clin.*, Vol. 45(3), pp. 165–178 (1995). Preferably, the radioactive salt is introduced substantially homogeneously in a tumor to minimize the occurrence in the tumor of cold (untreated) areas.

In certain preferred embodiments, the radioactive salt is administered in combination with a pharmaceutically acceptable carrier. A wide variety of pharmaceutically acceptable carriers are available and can be combined with the present radioactive salts. Such carriers would be apparent to one skilled in the art, based on the present disclosure. Of course, any material used as a carrier is preferably biocompatible. "Biocompatible", as used herein, refers to materials which are generally not injurious to biological functions and which will not result in any degree of unacceptable toxicity, including allergenic responses and disease states. Suitable carriers include, but are not limited to, water, buffer or saline solution. Other suitable carriers are described, for example, in Remington's, *Pharmaceutical Sciences*, Gennaro, A. R., ed., Mack Publishing Co., Easton, Pa. (1985), and *The United States Pharmacopeia*- The National Formulary, 22nd Revision, Mack Printing Company, Easton, Pa. (1990), the disclosures of each of which are hereby incorporated herein by reference, in their entirety.

The concentration of the radioactive salt employed in the pharmaceutical compositions and/or the amount of radioactive salt administered to the patient may vary and depends upon a variety of factors including, for example, the particular radioactive salt and/or pharmaceutically acceptable carrier employed, the particular disease being treated, the extent of the disease, the size and weight of the patient, and the like. Typically, the radioactive salt may be employed in the pharmaceutical compositions, and the compositions may be administered to a patient to provide initially lower levels of radiation dosages which may be increased until the desired therapeutic effect is achieved. Generally speaking, the radioactive salt may be employed in pharmaceutical compositions which comprise an aqueous carrier to provide a concentration of absolute radioactivity which may range from about 4 MBq per milliliter (mL) (about 0.1 mCi/mL)

or less to about 370 MBq/mL (about 10 mCi/mL), and all combinations and subcombinations of ranges therein. Preferably, the concentration of the radioactive salt in the pharmaceutical compositions may be from about 37 MBq/mL (about 1 mCi/mL) to about 370 MBq/mL (about 10 mCi/mL). In addition, the compositions may be administered to a patient to provide a radiation dose which may range from about 1 KSv (about $1 \times 10^5$ Rem) to about 74 KSv (about 7.4 MRem), and all combinations and subcombinations of ranges therein. Preferably, the compositions may be administered to a patient to provide a radiation dose of from about 7.4 KSv (about $7.4 \times 10^5$ Rem) to about 74 KSv (about 7.4 MRem). Such amounts are referred to herein as effective amounts or therapeutically effective amounts.

In certain preferred embodiments, the pharmaceutically acceptable carrier may further comprise a thickening agent. "Thickening agent", as used herein, refers to any of a variety of generally hydrophilic materials which, when incorporated in the present compositions, may act as viscosity modifying agents, emulsifying and/or solubilizing agents, suspending agents, and/or tonicity raising agents. Thickening agents which may be suitable for use in the present radiopharmaceutical compositions include, for example, gelatins, starches, gums, pectin, casein and phycocolloids, including carrageenan, algin and agar; semi-synthetic cellulose derivatives; polyvinyl alcohol and carboxyvinylates; and bentonite, silicates and colloidal silica. Exemplary of the foregoing materials are, for example, carbohydrates such as, for example, mannitol, glucose and dextrose, and the phosphorylated and sulfonated derivatives thereof; agarose; polyethers, including polyethers having a molecular weight of, for example, from about 400 to about 100,000; di- and trihydroxy alkanes and their polymers having a molecular weight of, for example, about 200 to about 50,000; acacia; diethanolamine; glycerol monostearate; lanolin alcohols; lecithin; mono- and diglycerides; monoethanolamine; oleic acid; oleyl alcohol; polyoxyethylene 50 stearate; polyoxyl 35 castor oil; polyoxyl 10 oleyl ether; polyoxyl 20 cetostearyl ether; polyoxyl 40 stearate; propylene glycol diacetate; propylene glycol monostearate; sodium stearate; stearic acid; trolamine; emulsifying wax; agar; alginic acid; aluminum monostearate; bentonite; magma; carbomer 934P; hydroxyethyl starch; carboxymethylcellulose; calcium and sodium and sodium 12; carrageenan; cellulose; dextran; gelatin; guar gum; locust bean gum; veegum; hydroxyethyl cellulose; hydroxypropylmethylcellulose; magnesium-aluminum-silicate; methylcellulose; pectin; polyethylene oxide; povidone; propylene glycol alginate; silicon dioxide; sodium alginate; tragacanth; xanthan gum; α-d-gluconolactone; glycerol; mannitol; polyethyleneglycol (PEG); polyvinylpyrrolidone (PVP); polyvinylalcohol (PVA); polypropylene glycol; polysorbate; sorbitol; propyleneglycol; glycerol; and polyoxyethylene-polyoxypropylene glycol block copolymers. Preferred among the polyoxyethylene-polyoxypropylene glycol block copolymers are α-hydroxy-ω-hydroxypoly(oxyethylene) poly(oxypropylene)-poly(oxyethylene) block copolymers. These latter block copolymers are generally referred to as poloxamer copolymers. Examples of poloxamer copolymers which may be particularly suitable for use in the present compositions include, for example, poloxamer F68, poloxamer L61 and poloxamer L64. These poloxamer copolymers are commercially available from Spectrum 1100 (Houston, Tex.).

Preferred among the thickening agents listed above are gelatins, polyvinylpyrrolidone and polyoxyethylene-polyoxypropylene glycol block copolymers. Other thickening agents, in addition to those exemplified above, would be apparent to one skilled in the art, based on the present disclosure.

The concentration of thickening agent, when present in the compositions of the present invention, may vary and depends upon various factors, including, for example, the particular thickening agent, radioactive salt, pharmaceutically acceptable carrier, and the like, employed. Preferably, the concentration of thickening agent is at least sufficient to impart desirable properties to the compositions, including, for example, a modification of the viscosity of the compositions. Generally speaking, the concentration of thickening agent may range from about 0.1 to about 500 milligrams (mg) per mL of pharmaceutical composition, and all combinations and subcombinations of ranges therein. Preferably, the concentration of thickening agent may be from about 1 to about 400 mg/mL, with concentrations of from about 5 to about 300 mg/mL being more preferred. Even more preferably, the concentration of thickening agent may be from about 10 to about 200 mg/mL, with concentrations of from about 20 to about 100 mg/mL being still more preferred. Especially preferred are concentrations of thickening agent of from about 25 to about 50 mg/mL.

Compositions which may be prepared from the radioactive salts, pharmaceutically acceptable carriers and optional thickening agents include, for example, suspensions, emulsions, and dispersions. Preferably, the radioactive salts may be formulated and administered to a patient as a suspension. "Suspension", as used herein, refers to a mixture, dispersion or emulsion of finely divided colloidal particles in a liquid. "Colloidal", as used herein, refers to a state of subdivision of matter which comprises particles of single large molecules or aggregations of smaller molecules. The particles may be sized microscopically and together comprise the dispersed phase. This dispersed phase is generally surrounded by different matter, generally referred to as the dispersion medium or external phase.

Suspensions may be obtained, for example, by combining the radioactive salt with an inert support material. "Inert", as used herein, refers to substances which are generally resistant to chemical or physical action. Preferably, the inert substances are also biocompatible. In preferred form, the inert support material is an adsorbent and/or absorbent solid on which the radioactive salt may be adsorbed and/or absorbed. In certain preferred embodiments, the inert solid may comprise particles, and more preferably, finely divided particles. Such support materials are referred to herein as "particulate support materials." Particulate support materials which may be suitable for use as an inert solid support in the compositions of the present invention include, for example, materials derived from carbon, including those forms of carbon typically referred to as carbon black (lampblack) and/or activated carbon, as well as finely powdered oxides, Kieselguhr, and diatomaceous earth. Preferably, the support material comprises carbon black or activated carbon.

The size of the particles of the particulate support material may vary and depends, for example, on the particular support material, radioactive salt, thickening agent, and the like, employed. Generally, the particulate support material may comprise particles ranging in size, for example, from about 0.1 micrometer ($\mu$m) to about 50 $\mu$m, and all combinations and subcombinations of ranges therein. Preferably, the particle size may be from about 0.5 to about 25 $\mu$m, with particle sizes of from about 1 to about 10 $\mu$m being more preferred. Even more preferably, the particle size of the particulate support material may be from about 2 to about 5 $\mu$m.

The radioactive salt may be adsorbed and/or absorbed onto the adsorbent and/or absorbent solid material by a variety of techniques well known to those skilled in the art. Suitable techniques include, for example, dissolution of a radioactive salt in an appropriate solvent, including aqueous solvents. This salt mixture may then be combined with the support material which is thereafter isolated, for example, by filtration, and dried to provide the radiolabelled support material. In embodiments which involve radioactive salts of pyrophosphoric acid, the support material may be combined, for example, with an aqueous acid solution of a radioactive salt of pyrophosphoric acid. In alternate embodiments, the support material may be combined with an aqueous solution of a radioactive salt of phosphoric acid. In these latter embodiments, the radioactive phosphoric acid salt which is adsorbed and/or absorbed on the support material may be converted to the corresponding radioactive salt of pyrophosphoric acid. Such conversion may involve, for example, dehydration of the phosphoric acid salt. Generally speaking, this dehydration may involve heating the radiolabelled inert material to a temperature and for a time to substantially convert the phosphoric acid salt to the corresponding pyrophosphoric acid salt. Suitable temperatures to which the radiolabelled material may be heated to achieve this conversion include, for example, temperatures of from about 500 to about 1100° C. This heating may be conducted under a variety of atmospheres, such as air or an inert atmosphere, for example, argon or nitrogen. The dehydration reaction is generally completed in less than about 5 hours. Other methods for formulating the radioactive salts with the support materials, in addition to the methods described herein, would be readily apparent based on the present disclosure.

It would be apparent to one of ordinary skill in the art, once armed with the present disclosure, that in connection with the methods for the preparation of the radioactive salts and/or radiopharmaceuticals of the present invention, the particular material obtained upon heating a salt of phosphoric acid may vary and depends, for example, on the particular temperature and the length of time involved in the conversion process. For example, heating a salt of phosphoric acid to higher temperatures, for example, about 1100° C., and/or heating a salt of phosphoric acid for extended periods of time, may result in a degree of dehydration which may be greater than that required to provide a salt of pyrophosphoric acid. Accordingly, increased dehydration may provide salts other than the pyrophosphate salts described above, including, for example, salts of polyphosphoric acid such as, for example, linear salts of polyphosphoric acid which may have the formula $[P_nO_{3n+1}]^{(n+2)-}$, branched salts of polyphosphoric acid, or cyclic salts of polyphosphoric acid which may have the formula $[P_nO_{3n}]^{n-}$. As with the salts of pyrophosphoric acid, the salts which may be provided by increased dehydration are generally substantially insoluble in aqueous media, including blood. Accordingly, these salts may also be employed in the methods and compositions of the present invention and, therefore, are contemplated to be within the scope of the present invention.

The amount of particulate support material which may be employed in the compositions may vary and depends, for example, on the particular support material, radioactive salt, thickening agent, and the like, employed. Generally speaking, the support material may be employed in the compositions to provide concentrations, after absorption and/or adsorption thereon of the radioactive salt, which may range from about 0.1 to about 100 mg/mL of the composition, and all combinations and subcombinations of ranges therein. Preferably, after absorption/adsorption thereon of the radioactive salt, the support material may be employed in an amount of from about 0.5 to about 90 mg/mL, with amounts of from about 1 to about 80 mg/mL, about 2 to about 70 mg/mL, about 3 to about 60 mg/mL or about 5 to about 50 mg/mL being more preferred.

In an alternate preferred embodiment of the present invention, the radioactive salts described herein may be administered in the form of a solid radiopharmaceutical matrix. "Matrix", as used herein, refers to a solid article of manufacture which comprises an outer substance substantially surrounding an inner substance. In preferred form, the radioactive salts of the present invention are included within the inner substance. A wide variety of materials are available for use as the inner and outer substances. Preferably, the inner and outer substances are composed of materials which are inert and, preferably, biocompatible. In preferred form, the matrices comprise a biocompatible sleeve which substantially surrounds a radiopharmaceutical composition. A wide variety of biocompatible sleeves are available for use in connection with the present matrices. Preferably, the sleeve is formulated from a biocompatible polymer such as, for example, aliphatic polymers, including polyethylene polymers, polymers formed by condensation reactions, such as, for example, polyester polymers, including polymers sold under the trademark Dacron® (DuPont Corp., Wilmington, Del.), fluorocarbon polymers, such as, for example, polytetrafluoroethylene polymers, including polymers sold under the trademark Teflon® (DuPont Corp., Wilmington, Del.), and organosilicon polymers, such as, for example, polymers sold under the trademark Silastic® (Dow Coming, Corp., Midland, Mich.).

Preferred among the polymers listed above are polyester polymers, especially polymers sold under the trademark Dacron® (DuPont Corp., Wilmington, Del.). Other polymers, in addition to those exemplified above, would be apparent to one skilled in the art, based on the present disclosure.

In the present matrices, the biocompatible sleeve preferably substantially surrounds a radiopharmaceutical composition. The radiopharmaceutical composition preferably comprises a radioactive salt of pyrophosphoric acid and one or more polymeric resins. Suitable radioactive salts of pyrophosphoric acid include those described in detail above such as, for example, the salts of formula (I). In preferred form, the polymeric resins included in the radiopharmaceutical compositions may be, for example, thermoplastic resins, such as polymeric resins of acrylic acid and derivatives thereof, including polymers of methacrylate resins and cyanomethacrylate resins, polymers formed by condensation reactions, such as, for example, polyester polymers, and thermosetting resins, such as, for example, epoxy resins.

Preferred among the resins listed above are epoxy resins, with modified epoxy resins sold under the trademark Araldite® GY 507 (Ciba Geigy Corp., Brawater, N.Y.) being particularly preferred. Other resins, in addition to those exemplified above, would be apparent to one skilled in the art, based on the present disclosure.

A wide variety of methods are available for preparing the matrices of the present invention. For example, a radioactive salt of pyrophosphoric acid may be combined with a suitable curable polymeric resin, such as an epoxy resin. To promote curing of the polymeric resin, including the epoxy resins described above, additional components may be incorporated, such as, for example, curing agents, hardening agents, and the like. Preferably, the resin further comprises a hardening agent. A particularly preferred hardening agent is Hardener HY 951, commercially available from Ciba Geigy Corp. (Brawater, N.Y.). The concentration of the radioactive salt employed may vary and depends upon a variety of factors including, for example, the particular radioactive salt and/or polymeric resins employed, the use of additional agents in the resin mixture, such as curing agents and/or hardening agents, the particular disease being treated, the extent of the disease, the size and weight of the patient, and the like. Typically, the radioactive salt may be employed in the polymeric resin or resins and, accordingly, the matrices, and the matrices may be administered to a patient to provide initially lower levels of radiation dosages which may be increased until the desired therapeutic effect is achieved. Generally speaking, the radioactive salt may be employed in a concentration of from greater than 0 to about 50%, and all combinations and subcombinations of ranges therein, based on the total weight of the resin or resins and optional curing or hardening agent employed. Preferably, the concentration of the radioactive salt is from about 0.5 to about 40%, with concentrations of from about 1 to about 30% being even more preferred. Even more preferably, the radioactive salt is employed in a concentration of from about 1.5 to about 20%, with a concentration of from about 2 to about 10% being still more preferred. Yet more preferably, the concentration of radioactive salt is from about 3 to about 5%, with a concentration of about 4% being particularly preferred.

The mixture of radioactive salt, polymeric resin, and optional additional ingredients may be blended until homogenous, and the resulting mixture may be introduced into the biocompatible sleeve, preferably a Dacron® sleeve, so that the sleeve substantially surrounds the radioactive resin mixture. The introduction of the resin mixture into the sleeve may be accomplished, for example, by pumping the mixture into the sleeve using an appropriate mechanical and/or vacuum pump. Suitable pumps for this purpose are readily available and would be apparent to one of ordinary skill in the art, based on the present disclosure. The particular pump employed may depend, for example, on a variety of factors, including the viscosity of the resinous mixture, as well as the dimensions of the sleeve employed, namely, its length and inner and outer diameters. The dimensions of the sleeve employed, in turn, may vary and depends upon a variety of factors including, for example, the particular radioactive salt and/or polymeric resins employed, the particular disease being treated, the extent of the disease, the size and weight of the patient, and the like. Generally speaking, the length of the sleeve employed may range from about 0.1 cm to about 5 cm, and all combinations and subcombinations of ranges therein. Preferably, the sleeve length may range from about 0.3 cm to about 3 cm, with a length of from about 0.8 cm to about 2 cm being more preferred. Even more preferably, the sleeve length may be about 1 cm. The external diameter of the sleeve may range from about 0.2 mm to about 2 mm, and all combinations of ranges therein. Preferably, the external diameter may range from about 0.5 mm to about 1.5 mm, with an external diameter of about 1 mm being preferred. The internal diameter of the sleeve may range from about 0.1 mm to about 1.8 mm, and all combinations of ranges therein. Preferably, the internal diameter may range from about 0.3 mm to about 1.3 mm, with an internal diameter of about less than about 1 mm, such as about 0.8 mm, being preferred.

In preferred form, after introduction into the sleeve, the resin mixture containing the radioactive salt is preferably cured to provide the present solid matrices. The curing method employed may vary and depends, for example, on the particular polymeric resin and optional curing and/or hardening agents employed. Generally speaking, the resin mixture may be cured, for example, by the application of heat or ultraviolet (UV) light, with heat curing being preferred. The resulting matrix may thereafter be administered to a patient, as described herein.

The present invention also provides convenient pharmaceutical kits. Such kits may comprise a radioactive salt of pyrophosphoric acid and, typically, a pharmaceutically acceptable carrier. The kit may also further comprise conventional kit components, such as needles for use in injecting the compositions, one or more vials for mixing the composition components, and the like, as will be apparent to those skilled in the art. In addition, instructions, either as inserts or as labels, indicating quantities of the components, guidelines for mixing the components, and protocols for administration, may be included in the kits.

The radioactive salts, radiopharmaceutical compositions and radiopharmaceutical matrices of the present invention provide surprising and unexpected results in the treatment of disease, such as carcinomas, in that they may resist mobilization and/or distribution in the bloodstream. Moreover, the present radioactive salts and radiopharmaceutical compositions and matrices may be highly efficacious for the treatment of cancers, especially prostate cancer. In connection with prostate cancer, it has been observed that patients suffering therefrom may exhibit a marked decrease in the levels of prostate-specific antigen (PSA) after administration of the present radioactive salts, compositions and/or matrices. As known to those skilled in the art, observation of PSA levels may be a preferred method for evaluating response of a particular treatment.

The invention is further described in the following examples. All of the examples are actual examples. These examples are for illustrative purposes only, and are not to be construed as limiting the appended claims.

EXAMPLE 1

This example describes the preparation of a radiopharmaceutical composition within the scope of the present invention.

A. Inert Support

Carbon black (2 g), having an active adsorption surface of about 450 m$^2$ per g, was suspended in analytical/pharmaceutical grade petroleum ether (40 mL). The suspension was centrifuged and the supernatant was decanted. This procedure was repeated, and the carbon black was subsequently washed with acetone (1×40 mL) and ethanol (2×40 mL). The carbon black was dried by heating in an oven (200° C.) for 24 hours. To the dried carbon black was added a 1% solution (25 mL) of potassium dichromate ($K_2Cr_2O_7$), with stirring, over a period of about 5 minutes. The resulting mixture was centrifuged, the supernatant was decanted and the carbon black was washed twice with bidistilled water. After the second washing, the carbon black was resuspended in a minimum volume of bidistilled water and transferred to a flask suitable for oven drying. The carbon black suspension was then dried in an oven (50° C) for 2 days, cooled and stored in a glass vial.

B. Radiolabeling of Inert Support

The carbon black material from Step A (50 mg) was introduced into a flexible, polyethylene tube. A carrier free solution of $^{32}$P labeled sodium orthophosphate, having an activity of about 2 mCi, and 0.02 N HCl was prepared. About 1 mL of this orthophosphate solution was added into the polyethylene tube. The mixture was dried in an oven (50 to 60° C.) for a period of about 24 hours. The dried material was transferred to a neutral glass vial, the opening of which was covered with a small porcelain or platinum capsule. The flask was heated in a sterile environment to a temperature of from about 550° C. to about 600° C. for a period of about 15 minutes, during which time the contents of the vial were maintained free of any foreign matter. During this heating phase, the carbon black developed a red hue. The mixture was cooled, and sterile stainless steel bearings or cylinders having a diameter of from about 1 mm to about 2 mm were introduced into the flask. The flask was covered with a sterile rubber plug, sealed and placed behind a lucite shielding. The dried mixture was stirred vigorously for about 30 minutes, after which about 5 mL of a sterile physiological solution (pharmaceutical grade NaCl (9 g) in injectable grade $H_2O$ (1000 mL) was added. The resulting mixture was homogenized by vigorous stirring for a period of about 5 minutes. The absolute activity of the mixture was measured in an ionization chamber calibrated for $^{32}P$. The flask was centrifuged at 500 to 600 rpm for a period of about 10 minutes. Using a sterile syringe, the supernatant was substantially removed and its activity was measured in an ionization chamber. The activity of the supernatant was negligible.

C. Addition of Pharmaceutically Acceptable Carrier

A 3% solution of bovine gelatin was sterilized by heating in an autoclave (121° C.) for a period of about 30 minutes. The solution was permitted to cool until lukewarm, and an aliquot (2 mL) of the gelatin solution was added to the radiolabeled charcoal from Step B. The resulting mixture was stirred vigorously for a period of about 5 minutes to provide a radiopharmaceutical composition of chromium $^{32}P$ pyrophosphate, carbon black and gelatin.

EXAMPLE 1A

Example 1 was repeated, except that the 3% bovine gelatin solution in Step C was replaced with a 15% solution of polyvinylpyrrolidone.

EXAMPLE 2

This example includes a description of chemical and physical analyses which were conducted on the radiopharmaceutical composition prepared in Example 1.

A. Radiochemical Purity Analysis

A sample of the radiopharmaceutical composition prepared in Example 1 was analyzed for radiochemical purity. This analysis was conducted using paper chromatography (Whatman Paper No. 1) and 0.1 N HCl as the mobile phase. The chromatograph was developed in about 35 to about 40 minutes. The radiolabeled charcoal had an $R_f$ of 0, whereas $^{32}P$ orthophosphate had an $R_f$ of about 0.8 to about 0.9. The chromatography paper was analyzed using radioautography and the areas of interest were measured using a Geiger-Muller (GM) tube. The radiochemical purity of the composition was determined to be greater than 95% as $^{32}P$ pyrophosphate. The concentration of $^{32}P$ orthophosphate was determined to be about 1%.

B. Physicochemical Analysis

A sample of the radiopharmaceutical composition prepared in Example 1 was analyzed for its physicochemical properties using optical microscopy and flux citometry, the latter of which involved light scattering with a 500 mW argon laser. These analyses revealed that 90% of the particles in the radiopharmaceutical composition possessed a mean diameter of between about 2.5 and about 4 μm.

C. Stability Analysis

The stability of the radiopharmaceutical composition prepared in Example 1, as a function of time, was studied utilizing the paper chromatography technique described in paragraph A above. This study indicated that the amounts of $^{32}P$ pyrophosphate and $^{32}P$ orthophosphate remained constant over a period of at least about 1 month.

EXAMPLE 3

This example includes a description of preliminary toxicity and pyrogenicity studies which were conducted utilizing the corresponding non-radiolabeled form ($^{31}P$) of the radiopharmaceutical compositions of the present invention.

A. Preparation of $^{31}P$ Pyrophosphate Composition

Example 1 was repeated, except that the non-radiolabeled form of the orthophosphate salt was utilized in Step B.

B. Toxicity and Pyrogenicity Studies

The non-radioactive composition (1 mL) prepared in Step A was injected intraperitoneally into ten Sprague-Dawley rats. No toxicity was observed.

Following the procedure set forth in the Argentine Pharmacopea, VI Edition, a lukewarm solution of gelatin (3%) or polyvinylpyrrolidone (15%) was injected into the marginal vein of the ear of 3 rabbits. No pyrogenicity was observed.

EXAMPLE 4

This example describes prior art radiopharmaceutical compositions. The prior art compositions are as follows: (A) a composition of chromic $^{32}P$ orthophosphate and gelatin comprising particles having a mean particle size of from about 10 to about 30 nanonmeters (nm); (B) a composition of chromic $^{32}P$ orthophosphate and gelatin comprising particles having a mean particle size of from about 30 to about 70 nm; and (C) Phosphocol™ (Mallinckrodt Medical), which is a composition of chromic $^{32}P$ orthophosphate and dextrose (30%) comprising particles having a mean particle size of from about 0.5 to about 4 μm, with 90% of the particles having a mean particle size of from about 0.6 to about 2 μm.

The following examples include descriptions of in vivo pharmacological test procedures in animals which are believed to correlate to therapeutic activity in humans and other animals, and pharmacological test procedures in humans. The test procedures included a comparison of the amounts of radioactivity eliminated (referred to herein as "biological elimination") in the urine and feces of rats which were administered the compositions of the present invention and compositions of the prior art. The test procedures also included a comparison of the distribution of radioactivity in various tissues in the rats. The test procedures further included a comparison of the efficacy for the treatment of cancer of radioactive compositions within the scope of the present invention to the efficacy for the treatment of cancers of radioactive materials of the prior art.

EXAMPLE 5

This example describes experimental protocols involved in certain of the in vivo pharmacological test procedures.

A. Inducement of Cancers

Multiple mammary adenocarcinomas were induced in Sprague-Dawley female rats by the administration thereto of N-nitroso-N-methylurea (NMU) according to the methods described in Gullino et al., *Natl. Cancer Inst.* Vol. 54, pp. 401–404 (1975), and modified in Rivera et al., *Cancer Lett.*, Vol. 86, pp. 223–228 (1994). The NMU was administered at rat lifetimes of 50, 80 and 110 days. The mean latency period was 82 days, and the mean tumor incidence was 96%. Most of the tumors also developed metastasis.

B. Administration of Radioactive Materials

Tumors induced in the rats were identified, and the sizes of the tumors were measured with a caliper along two axes to substantially localize the geometrical center of the tumor. The area around the tumor was substantially depilated. From about 0.6 to about 1 mL of radioactive material was injected into the tumor to provide an injected activity of from about 0.6 to about 1 mCi. To minimize tissue destruction, the radioactive material was injected slowly through a fine needle. In addition, the needle was removed slowly after the injection was completed to permit the tissue to collapse, thereby avoiding reflux of the radioactive materials. The tumors which were treated with the radioactive compositions are referred to hereinafter as "treated tumors." The tumors which were not treated with radioactive compositions are referred to hereinafter as "control tumors."

At the conclusion of the experiments, the rats either died due to the growth of the control tumors or were sacrificed. The organs, bones and the treated tumors were removed, disrupted and mineralized with sulfochromic mixture. The radioactivity of the collected urine, feces, organs, bones, treated tumors, and $^{32}P$ standard were measured in a monochannel gamma spectrometer with an ordinary well crystal of INa(Tl) measuring 2"×2" and using the Bremsstrahlung photons of $^{32}P$ The counter was calibrated previously and the geometry of all of the measurements was maintained constant. The efficiency of the measurements was about 0.1%.

Unless indicated otherwise, the rats were kept in stainless steel metabolic cages which permitted the collection and separation of feces and urine during the in vivo experiments. Food and water were available to the rats at all times.

In the following examples, the radioactivity of the collected urine and feces was analyzed and is expressed as the "Eliminated Activity." The term "Eliminated Activity" is expressed as a percentage of the amount of radioactivity in the urine and feces, relative to the total amount of radioactivity injected into the experimental animal.

EXAMPLE 6

This example includes a description of biological elimination test procedures involving radiopharmaceutical compositions of the present invention.

Biological elimination tests were conducted and involved the administration of the composition of Example 1 to a total of 28 rats, referred to hereinafter as "Test 6." The results of Test 6 are set forth in the following Table 1 and are depicted graphically in FIG. 1.

TABLE 1

| Test | Length of Treatment (days) | Eliminated Activity (%) | | |
|---|---|---|---|---|
| | | Urine | Feces | Total |
| 6 | 32 | 8.3 ± 1.8 | 4.4 ± 3.5 | 12.7 ± 3.9 |

Inspection of Table 1 and FIG. 1 reveals that a substantially small amount of the radioactivity administered using the compositions of the present invention was eliminated from the body. In Test 6, the activity in the collected urine was substantially higher than the activity in the collected feces.

EXAMPLE 7

This example includes a description of biological elimination test procedures involving radioactive compositions of the prior art.

A. Biological Elimination Test Procedures Involving the Composition of Example 4(A)

Biological elimination tests were conducted and involved the administration of the composition of Example 4(A) to 14 rats, referred to hereinafter as "Test 7(A)." The results of Test 7(A) are set forth in the following Table 2 and are depicted graphically in FIGS. 2A to 2E.

TABLE 2

| Test | Sample | Length of Treatment (days) | Number of Animals | Eliminated Activity (%) | | |
|---|---|---|---|---|---|---|
| | | | | Urine | Feces | Total |
| 7A | (i) | 32 | 10 | 19.0 ± 3.6 | 32.7 ± 4.8 | 51.7 ± 6.9 |
| 7A | (ii) | 17 | 1 | 10.2 | 70.1 | 30.3 |
| 7A | (iii) | 28 | 1 | 9.8 | 79.5 | 89.3 |
| 7A | (iv) | 26 | 1 | 8.6 | 64.6 | 73.2 |
| 7A | (v) | 18 | 1 | 9.3 | 59.4 | 68.7 |

Figure 2A:
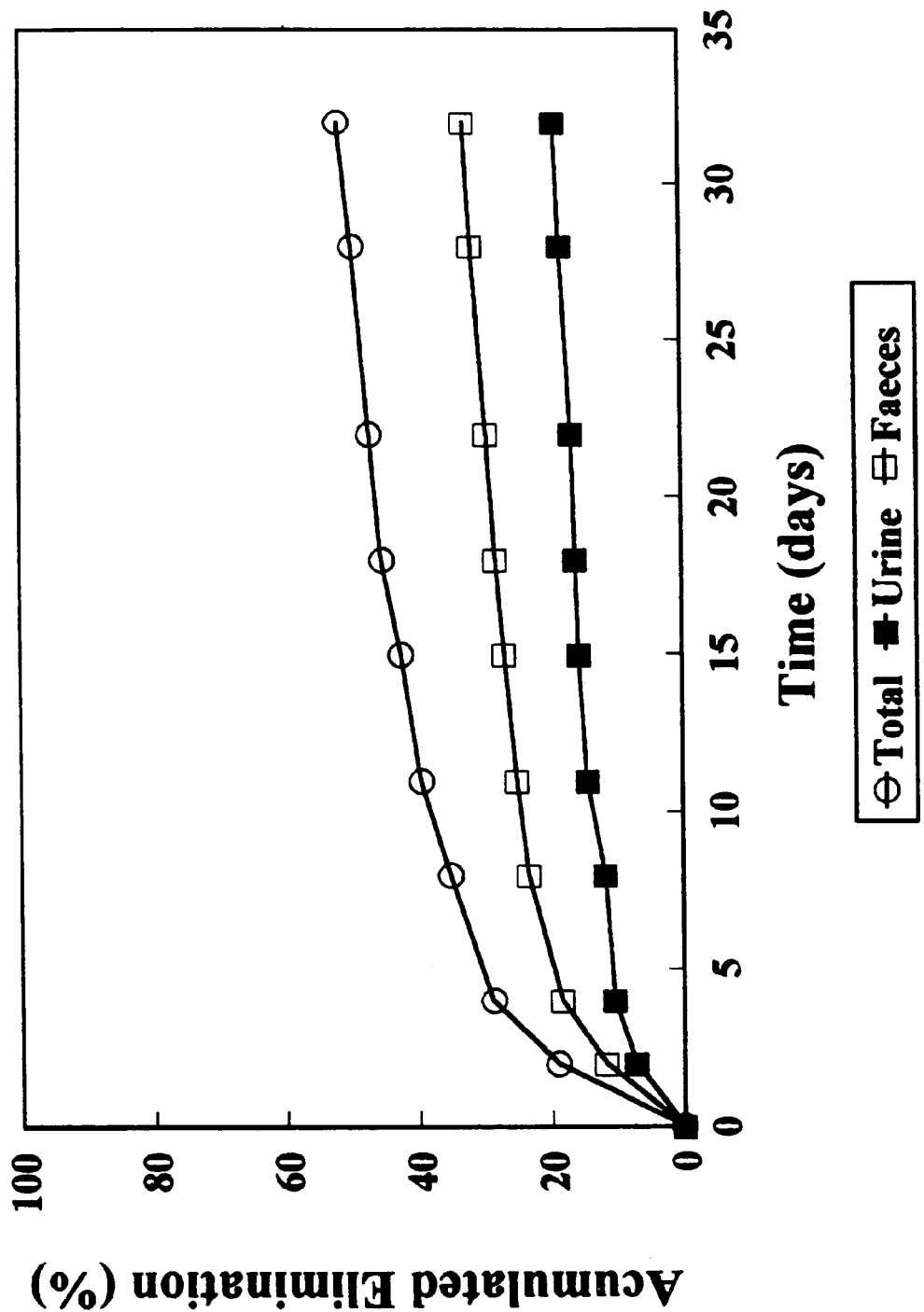
FIGS. 2A, 2B, 2C, 2D, 2E, 3A, 3B, 3C, 4A, 4B, 4C, 4D and 4E are graphical representations of studies of the biological elimination of radioactive materials according to the prior art.
Figure 2B:
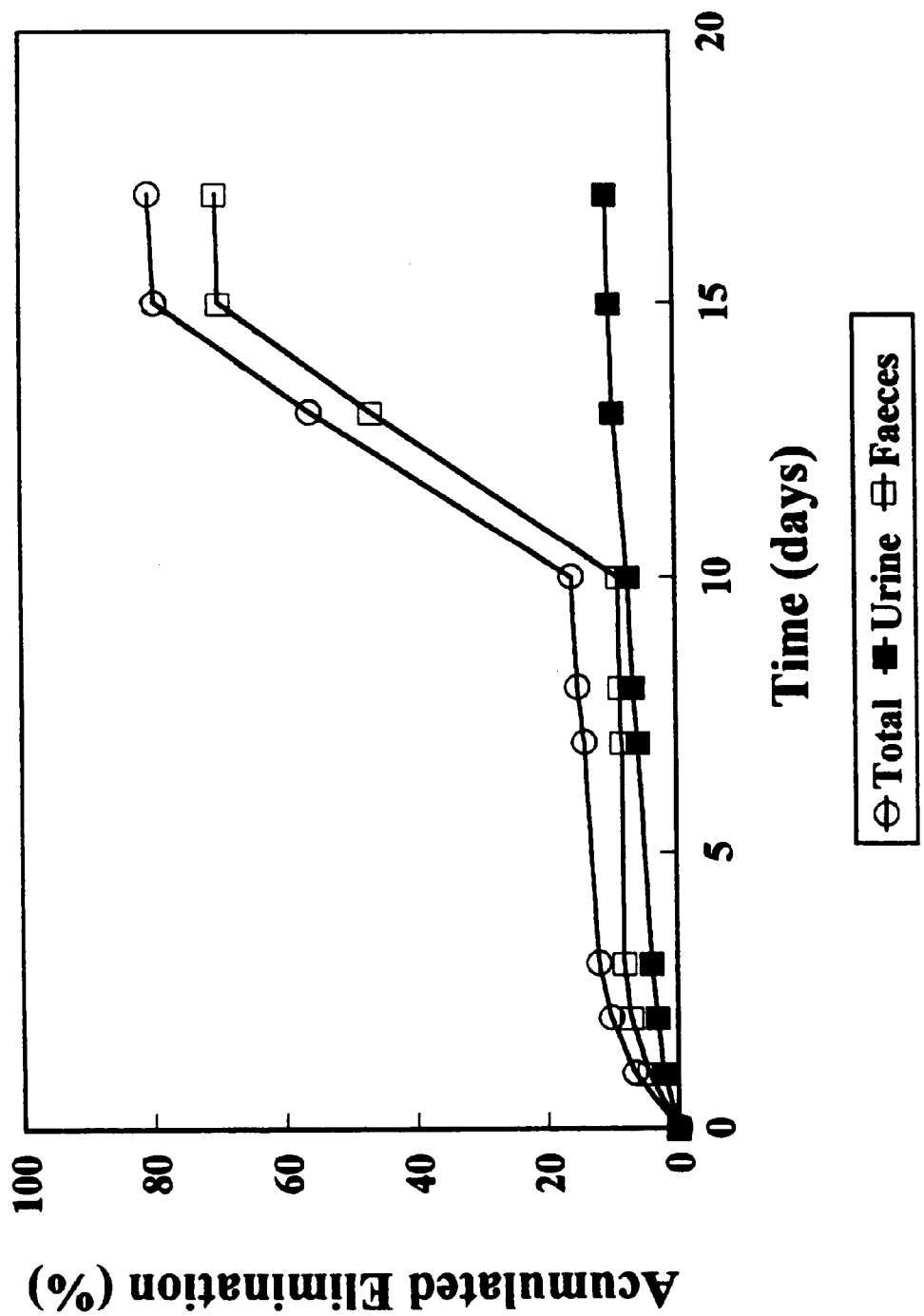
Figure 2C:
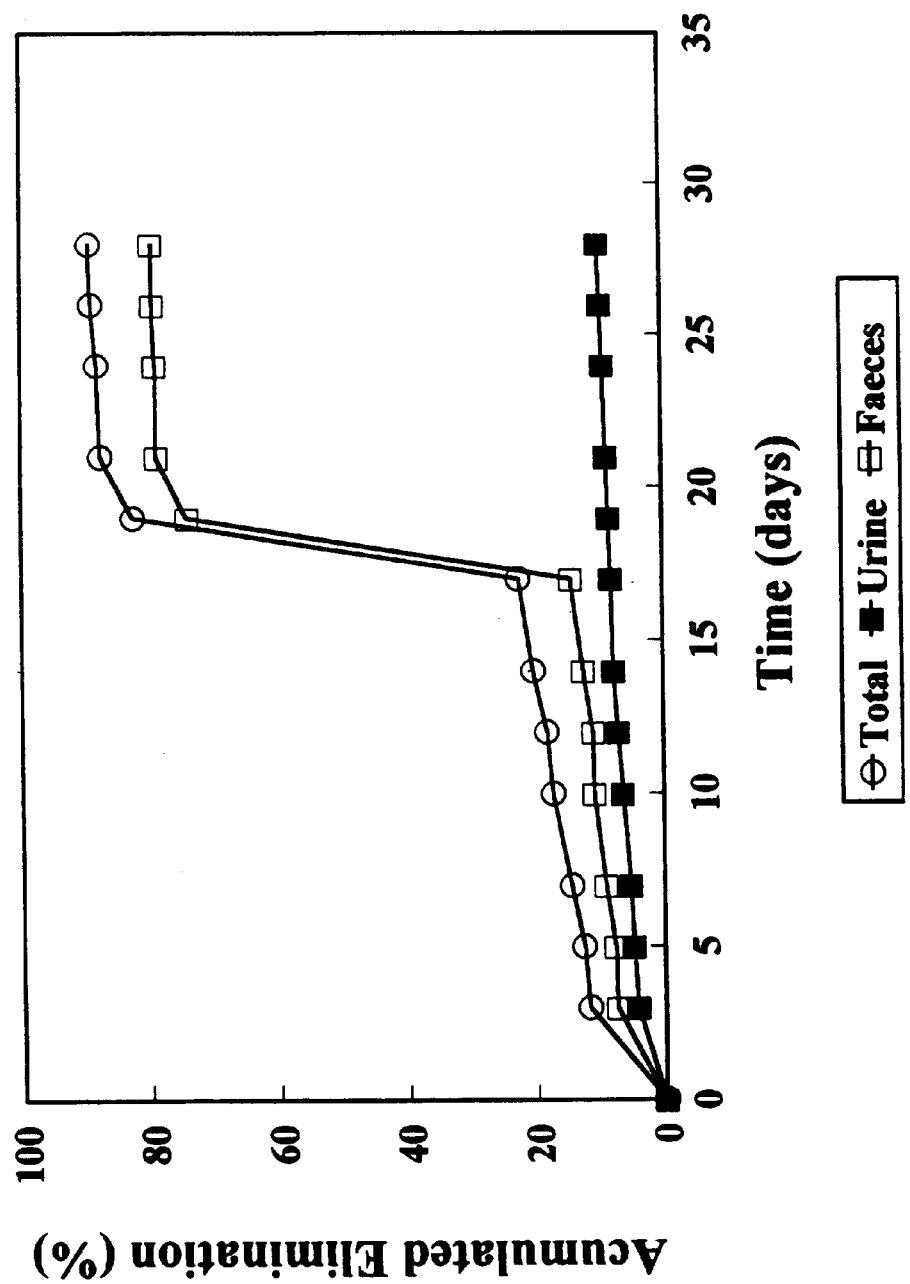
Figure 2D:
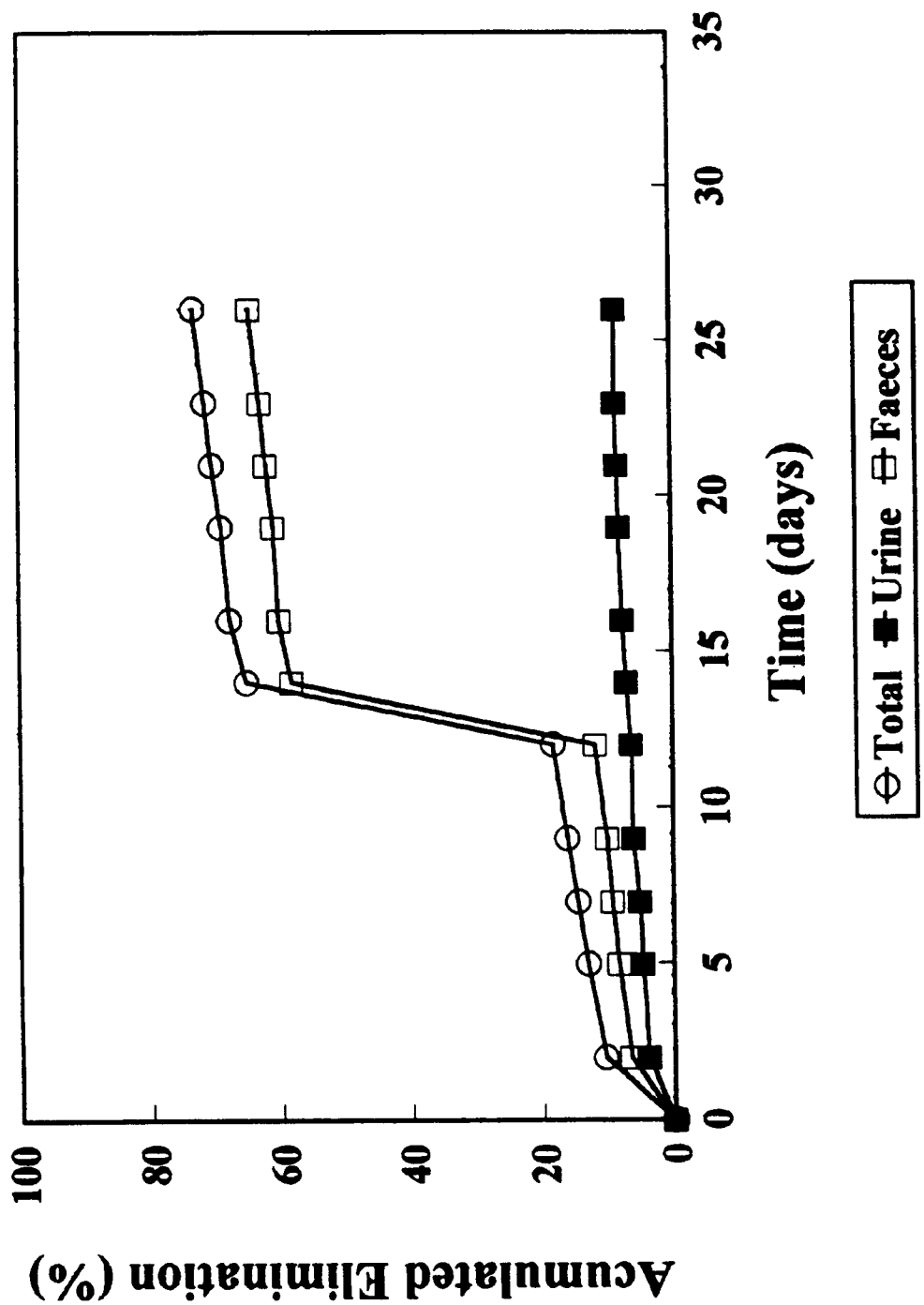
Figure 2E:
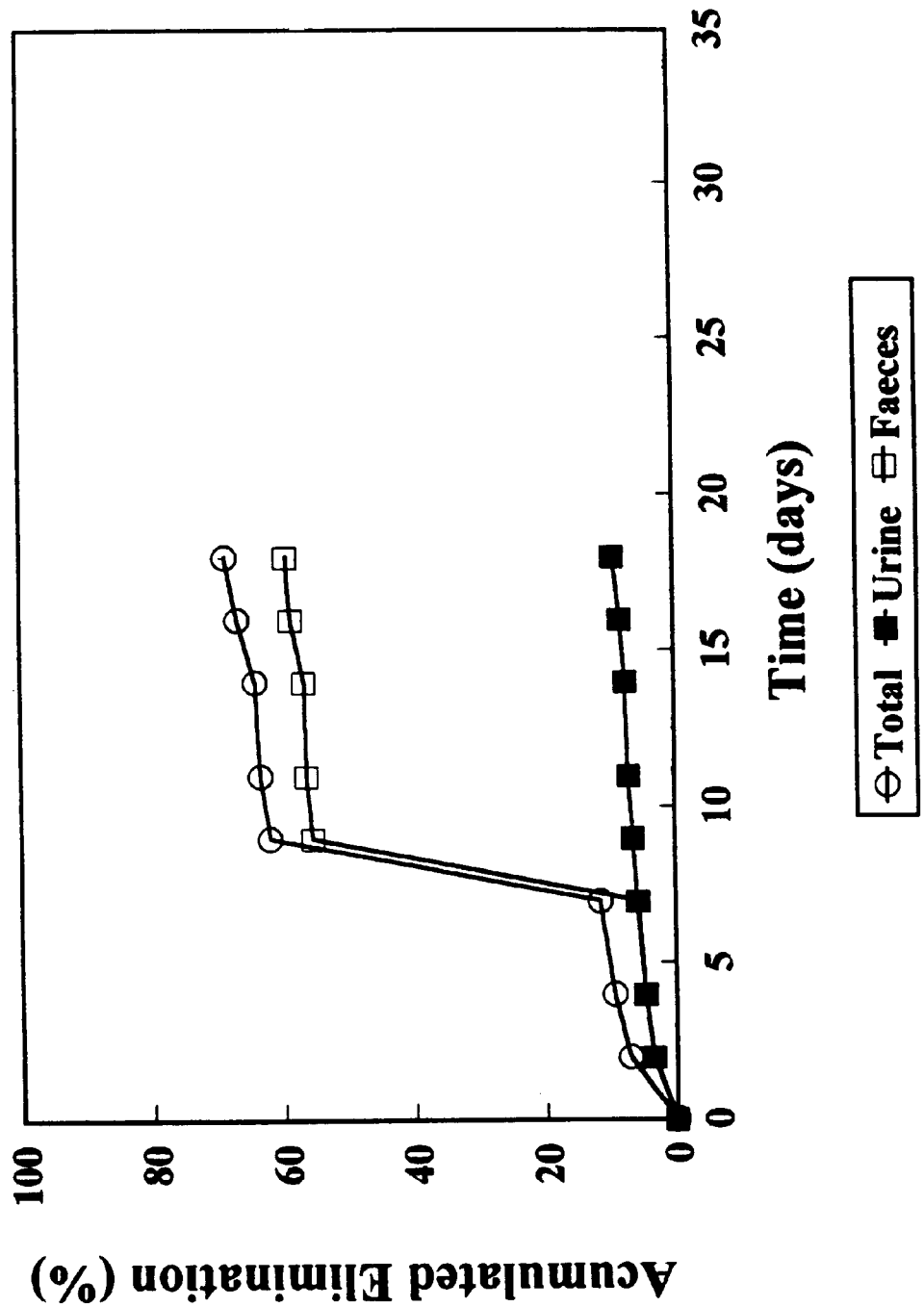

Test Sample 7(A)(i) and FIG. 2A show the eliminated activity for 10 of the treated animals as mean±standard deviation. Each of Test Samples 7(A)(ii) to 7(A)(v) and the corresponding figures (FIGS. 2B to 2E, respectively) show the eliminated activity for individual animals.

Inspection of Table 2 above and FIGS. 2A to 2E reveals that the eliminated radioactivity using a radioactive composition of the prior art (Example 4(A)) is significantly greater than the eliminated activity for the radioactive compositions of the present invention. It is believed that the increased elimination is due, at least in part, to the increased solubility in the bloodstream of the radioactive compositions of Example 4(A). This increased solubility results in enhanced mobilization of the compositions in the bloodstream, resulting in phagocytosis by the liver and eventual hydrolysis and excretion from the body. Inspection of Table 2 and FIGS. 2A to 2E also reveals that the eliminated activity was not reproducible, and differed significantly between test samples. Table 2 and the related figures also generally show a rise in the eliminated activity throughout the course of the test procedures.

B. Biological Elimination Test Procedures Involving the Composition of Example 4(B)

Biological elimination tests were conducted and involved the administration of the composition of Example 4(B) to 14 rats, referred to hereinafter as "Test 7(B)." The results of Test 7(B) are set forth in the following Table 3 and are depicted graphically in FIGS. 3A, 3B and 3C.

TABLE 3

| Test | Sample | Length of Treatment (days) | Number of Animals | Eliminated Activity (%) | | |
|---|---|---|---|---|---|---|
| | | | | Urine | Feces | Total |
| 7B | (i) | 32 | 12 | 6.84 ± 2.21 | 29.44 ± 5.26 | 36.28 ± 6.27 |
| 7B | (ii) | 32 | 1 | 8.3 | 56.7 | 65 |
| 7B | (iii) | 31 | 1 | 10.2 | 49.9 | 60.1 |

Figure 3A:
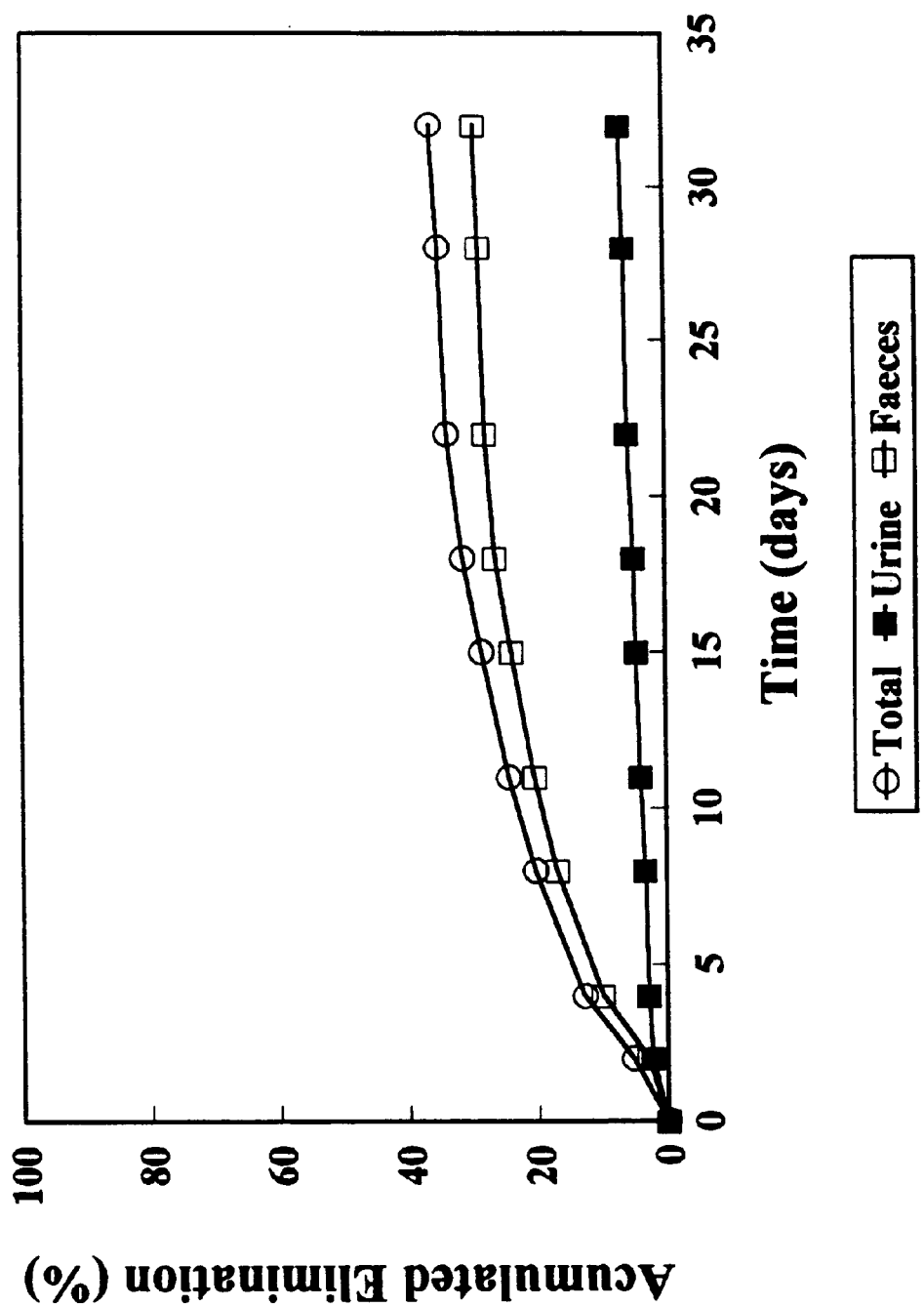

Test Sample 7(B)(i) and FIG. 3A show the eliminated activity for 12 of the treated animals as mean±standard deviation. Each of Test Samples 7(B)(ii) and 7(B)(iii) and the corresponding figures (FIGS. 3B and 3C, respectively) show the eliminated activity for individual animals.

Figure 3B:
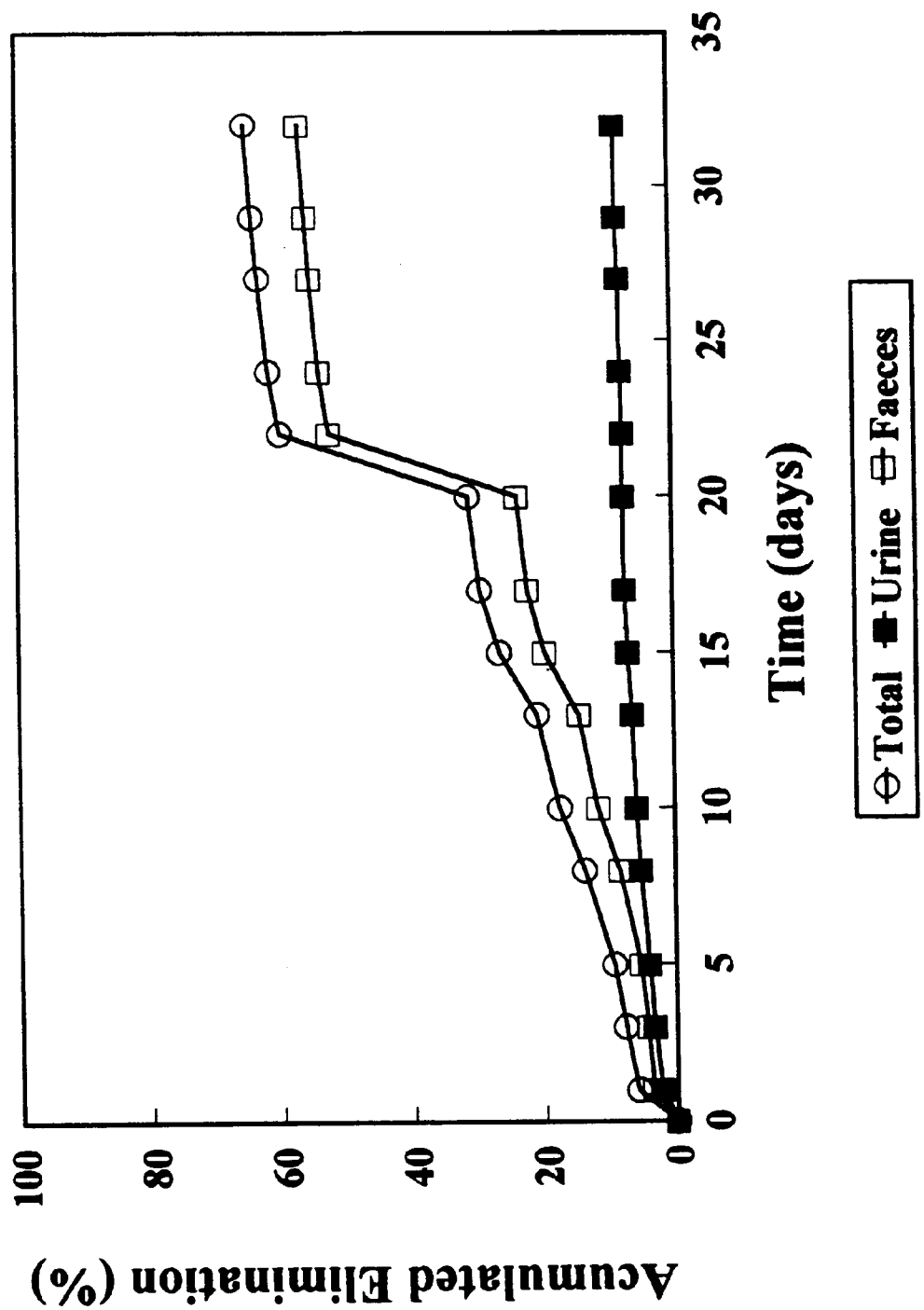
Figure 3C:
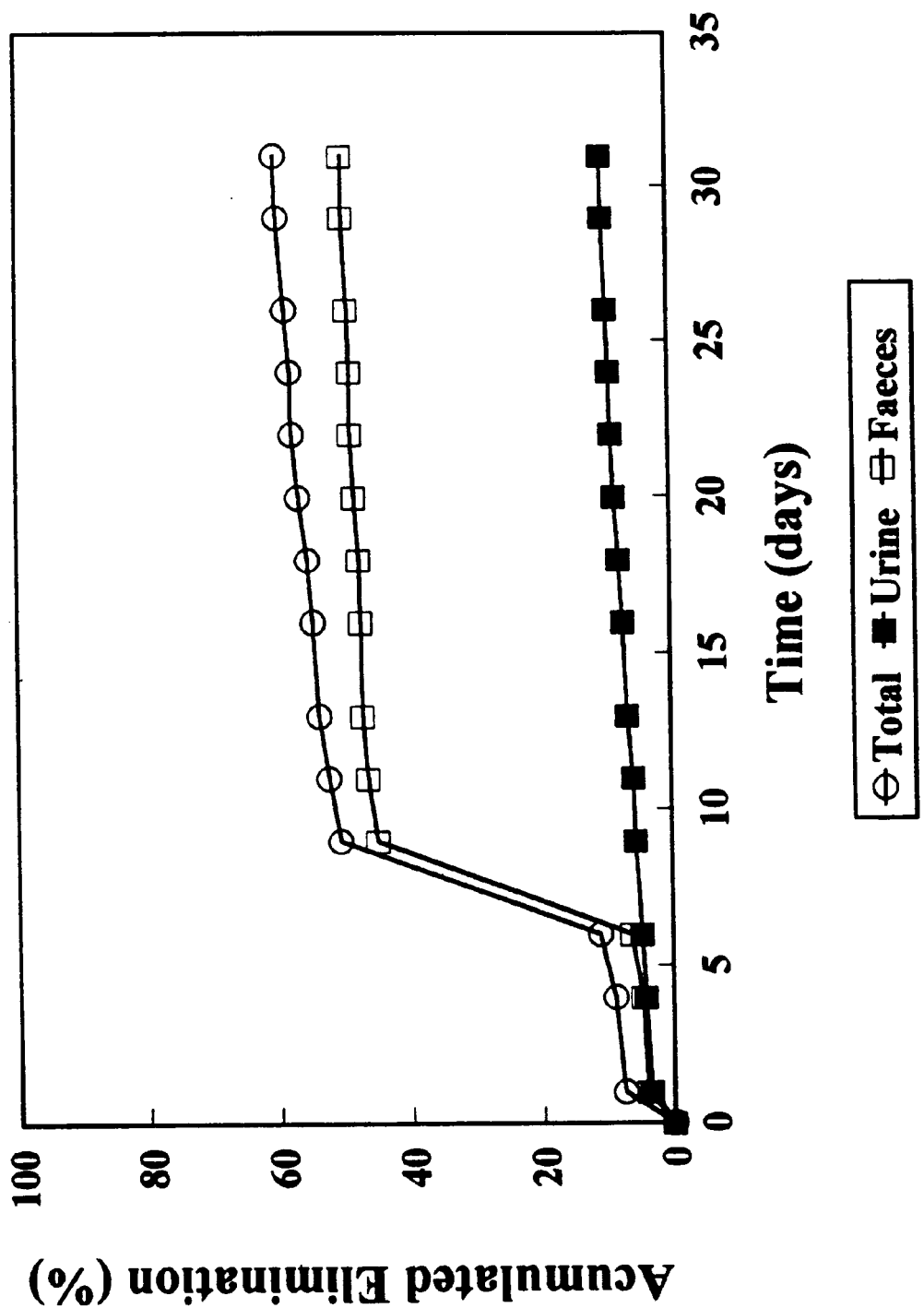

Inspection of Table 3 and FIGS. 3A, 3B and 3C reveals that greater than 35% of the radioactivity injected was eliminated using the composition of Example 4(B). This is an undesirably high amount of eliminated radioactivity and indicates that the prior art composition of Example 4(B) has a high degree of solubility in blood. Table 3 and the related figures also generally show a rise in the eliminated activity throughout the course of the test procedures.

C. Biological Elimination Test Procedures Involving the Composition of Example 4(C)

Biological elimination tests were conducted and involved the administration of the composition of Example 4(C) to 28 rats, referred to hereinafter as "Test 7(C)." The results of Test 7(C) are set forth in the following Table 4 and are depicted graphically in FIGS. 4A to 4E.

TABLE 4

| Test | Sample | Length of Treatment (days) | Number of Animals | Eliminated Activity (%) | | |
|---|---|---|---|---|---|---|
| | | | | Urine | Feces | Total |
| 7C | (i) | 32 | 24 | 6.48 ± 2.11 | 23.28 ± 8.81 | 29.76 ± 9.60 |
| 7C | (ii) | 32 | 1 | 6.4 | 50.01 | 56.41 |
| 7C | (iii) | 31 | 1 | 7.86 | 62.62 | 70.48 |
| 7C | (iv) | 30 | 1 | 8.99 | 89.19 | 98.18 |
| 7C | (v) | 29 | 1 | 14.81 | 63.73 | 78.54 |

Figure 4A:
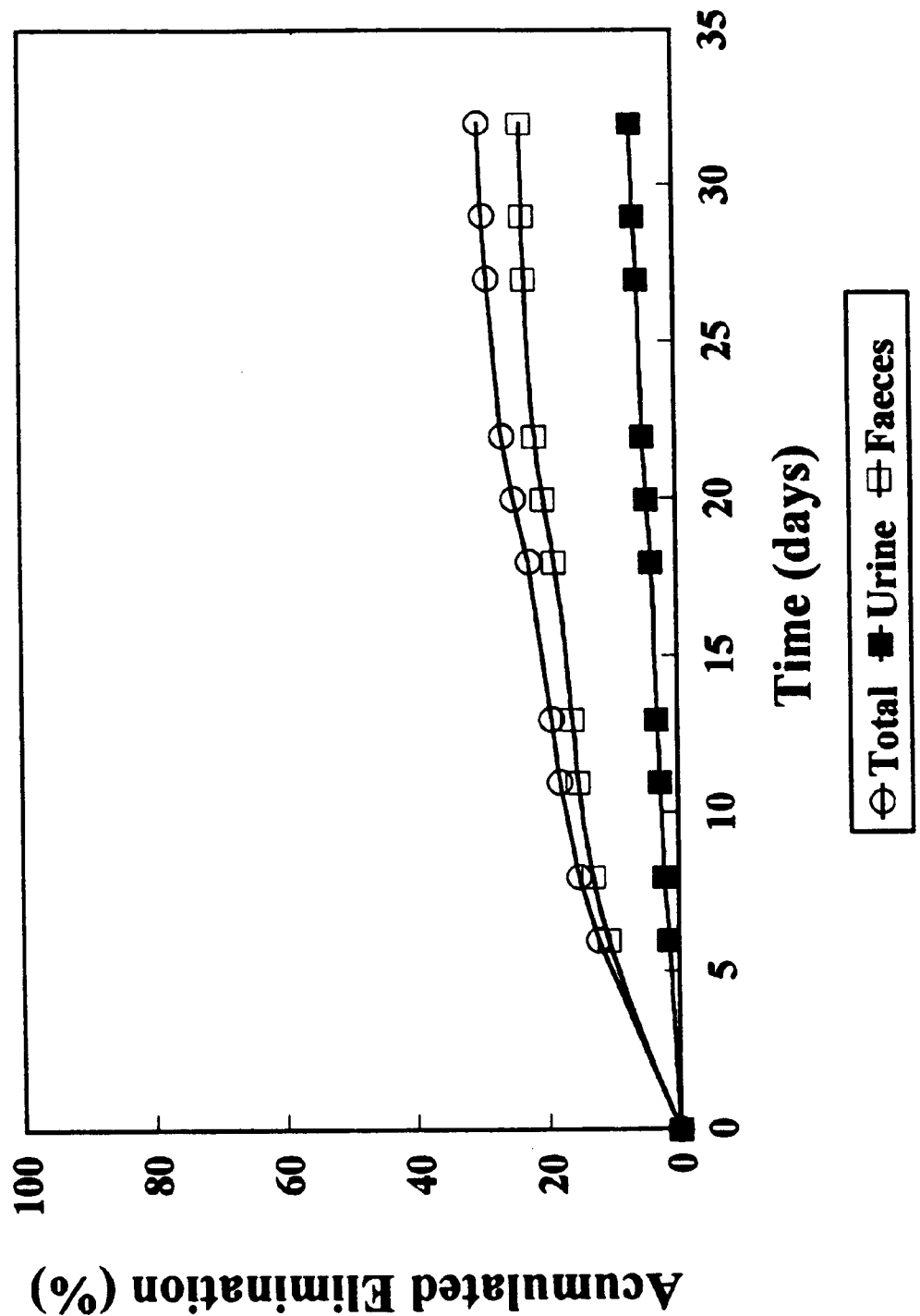
Figure 4B:
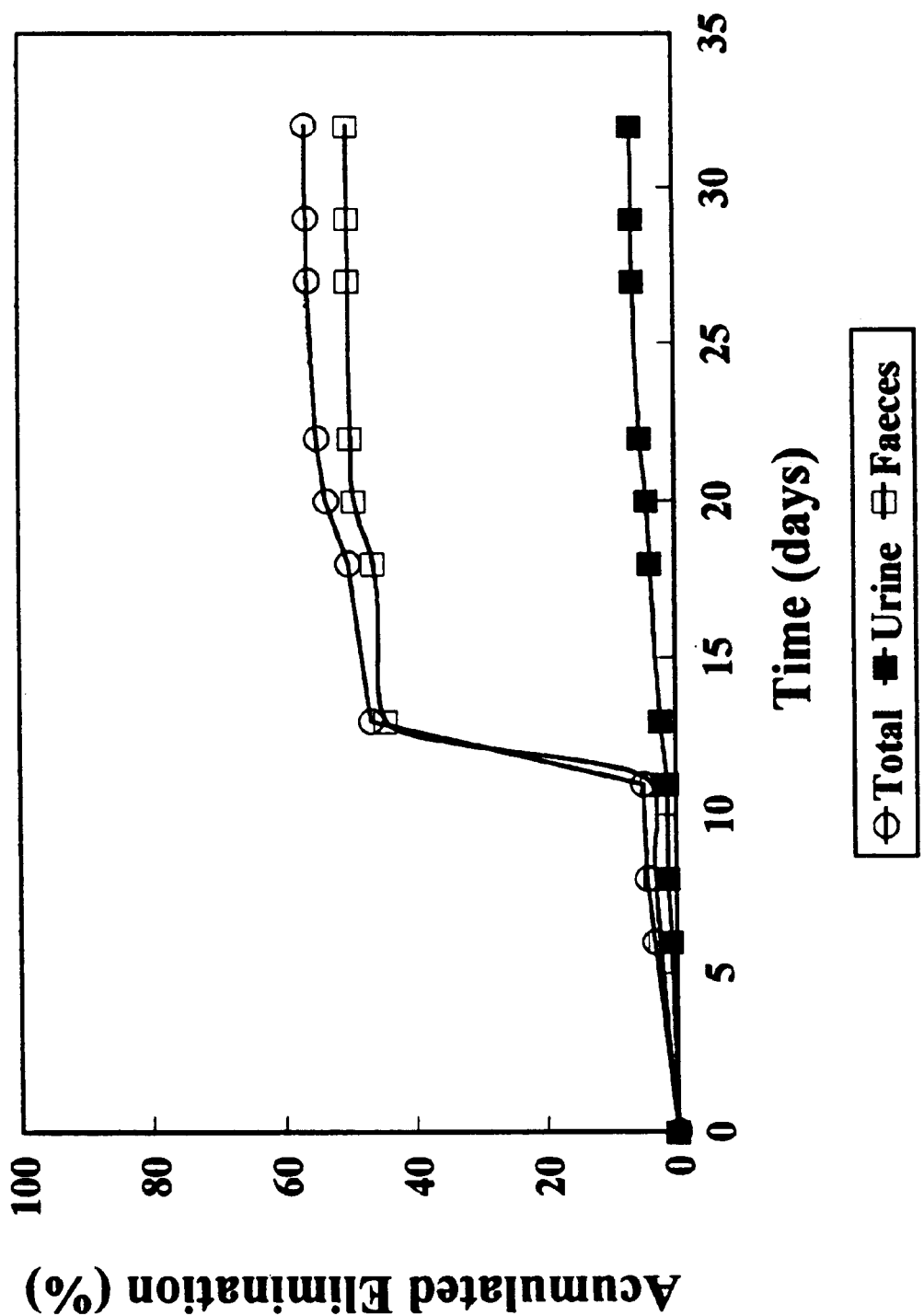
Figure 4C:
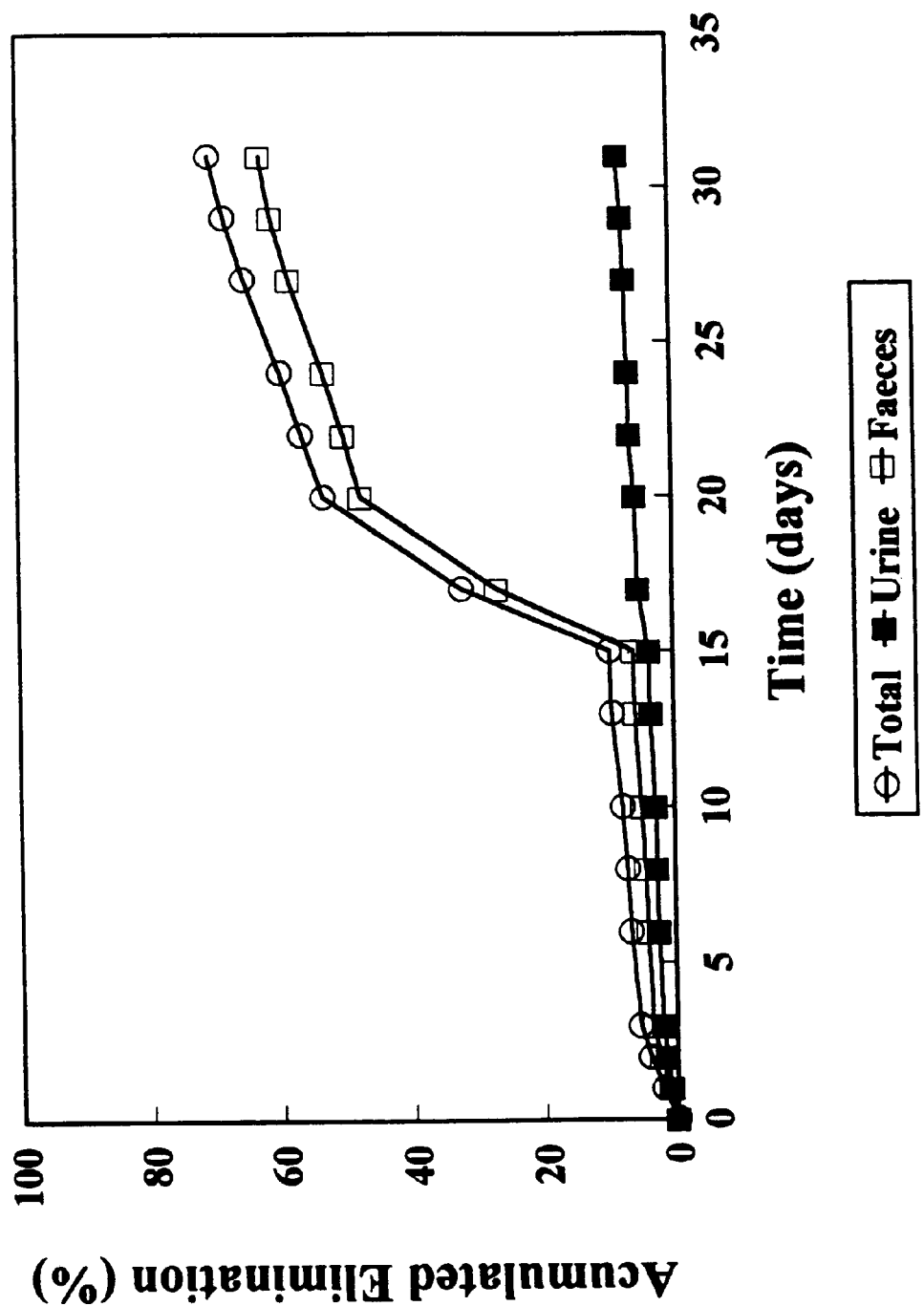
Figure 4D:
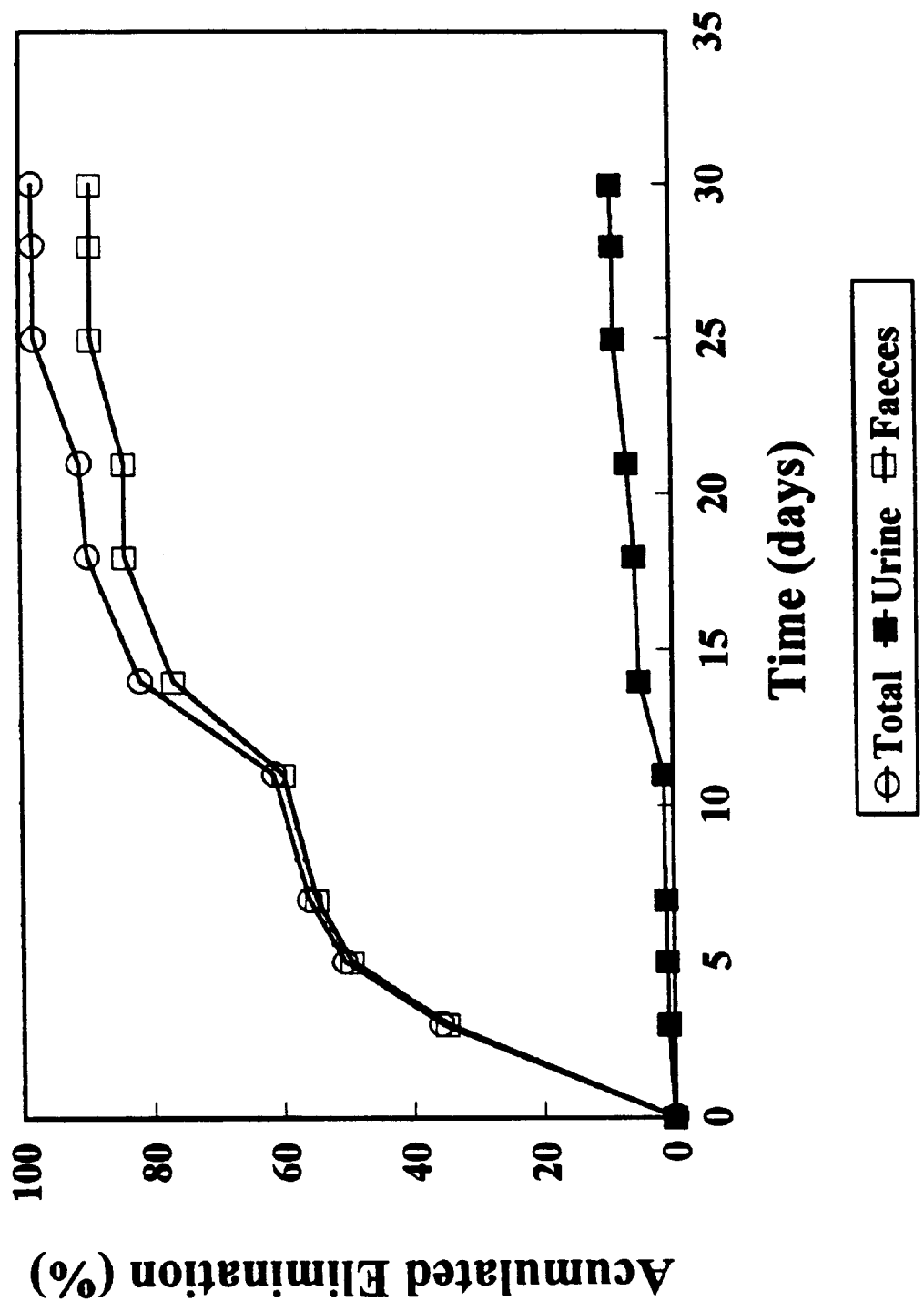
Figure 4E:
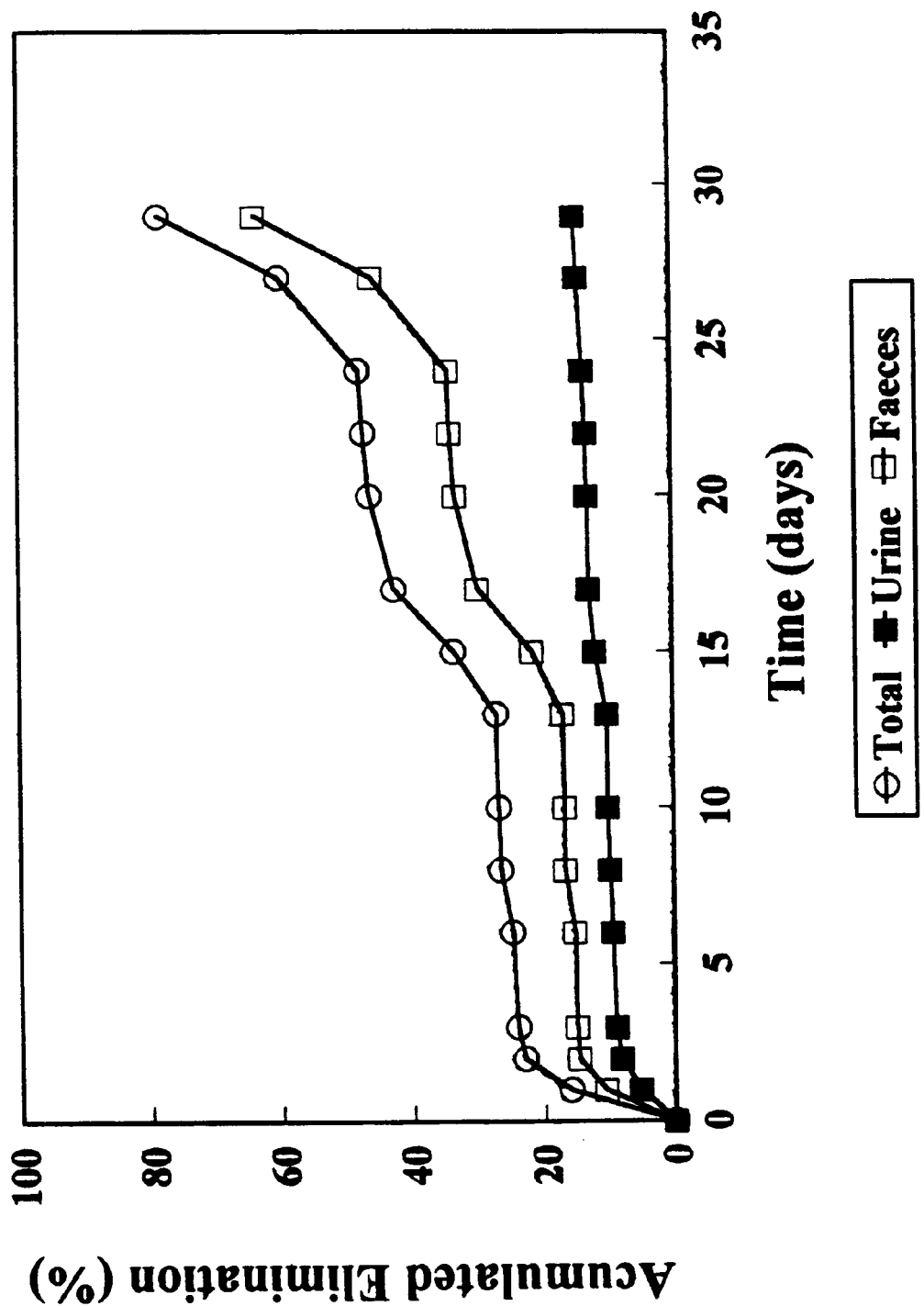

Test Sample 7(C)(i) and FIG. 4A show the eliminated activity for 24 of the treated animals as mean±standard deviation. Each of Test Samples 7(C)(ii) to 7(C)(v) and the corresponding figures (FIGS. 4B to 4E, respectively) show the eliminated activity for individual animals.

Inspection of Table 4 and FIGS. 4A to 4E reveals that the eliminated radioactivity varied from about 30% to as high as about 98%. Thus, the eliminated activity was substantially non-reproducible and differed dramatically between test samples. Table 4 and the related figures also generally show a rise in the eliminated activity throughout the course of the test procedures.

EXAMPLE 8

This example includes a comparison of the ability of the radiopharmaceutical compositions of the present invention and that of compositions of the prior art to remain in the treated tumors. This comparison involved an analysis of the biological distribution of radioactivity in the injected tumors, as well as in other tissues in the experimental animal, particularly the bone, liver, spleen, kidney and lung. The biological distribution test procedures described in this example are set forth below in Table 5. The biological test identified in Table 5 below as "Test 8(A)" involved the administration of the composition of Example 1. The biological tests identified in Table 5 as "Tests 8(B), 8(C) and 8(D)" involved the prior art compositions of Examples 4(A), 4(B) and 4(C), respectively.

The numerical values in Table 5 represent percentages of radioactivity in the involved tissue, based on the total amount of radioactivity injected in the tumor of the animal. The balance of the percentage of the total radioactivity measured generally corresponded to eliminated activity.

TABLE 5

| Test | Number of Animals | Injected Activity Per Organ (%) | | | | | |
|---|---|---|---|---|---|---|---|
| | | Tumor | Bone | Liver | Spleen | Kidney | Lung |
| 8A | 28 | 84.5 ± 2.6 | 1.20 ± 0.32 | 0.40 ± 0.15 | 0.80 ± 0.03 | 0.10 ± 0.03 | 0.08 ± 0.02 |
| 8B | 10 | 28.93 ± 1.3 | 1.26 ± 0.60 | 19.01 ± 1.30 | 0.52 ± 0.29 | 0.28 ± 0.11 | 0.29 ± 0.10 |
| 8C | 12 | 49.82 ± 5.41 | 1.91 ± 0.95 | 9.63 ± 4.89 | 1.16 ± 0.52 | 0.30 ± 0.11 | 2.54 ± 1.15 |
| 8D | 24 | 51.61 ± 5.82 | 1.38 ± 0.72 | 13.09 ± 5.15 | 1.39 ± 0.61 | 0.01 ± 0.01 | 2.88 ± 1.23 |

Inspection of Table 5 reveals that radioactivity administered to a tumor using compositions of the present invention substantially remains in the tumor, with negligible transport to other tissues. See Test 8(A) in Table 5. In contrast, substantial amounts of radioactivity administered to a tumor using prior art compositions fail to remain in the tumor and instead are transported to other bodily tissues. See Tests 8(B), 8(C) and 8(D).

Additional biological distribution tests were conducted to compare the ability of the radiopharmaceutical compositions of the present invention to that of compositions of the prior art to remain in the treated tumors. These additional biological distribution test procedures are set forth below in Table 6. The biological test identified in Table 6 below as "Test 8(E)" involved the administration of the composition of Example 1. The biological test identified in Table 6 as "Test 8(F)" involved the prior art composition of Example 4(B), and the biological tests identified in Table 6 as "Tests 8(G) and 8(H)" involved the prior art composition of Example 4(C).

TABLE 6

| Test | Number of Animals | Injected Activity Per Organ (%) | | | | | |
|---|---|---|---|---|---|---|---|
| | | Tumor | Bone | Liver | Spleen | Kidney | Lung |
| 8E | 6 | 89.9 ± 3.8 | 0.7 ± 0.2 | 1.5 ± 0.8 | 0.71 ± 0.3 | 0.8 ± 0.2 | 0.9 ± 0.2 |
| 8F | 1 | 58.2 | 3.2 | 0.6 | 0.3 | 0.3 | 0.3 |
| 8G | 1 | 91.6 | 0.2 | 2.4 | 0.14 | 0.01 | 0.48 |
| 8H | 1 | 1.0 | 0.3 | 0.11 | 0.05 | 0.05 | 0.15 |

Inspection of Table 6 reveals that the compositions of the present invention provide reproducible biological distributions. See Tests 8(E) and 8(A). However, the distributed radioactivity was substantially non-reproducible and differed dramatically in test samples involving the prior art compositions. See Tests 8(F) and 8(C); and Tests 8(G), 8(H) and 8(D).

EXAMPLE 9

Test procedures were conducted to evaluate the biological efficacy of the compositions of the present invention and the biological efficacy of compositions of the prior art. These tests generally involved injecting tumors with a radioactive composition and measuring the size of the tumors at regular intervals. The results of the tests are depicted graphically in FIGS. 5A, 5B, 5C and 5D.

A. Biological Efficacy of Compositions of the Present Invention

Figure 5A:
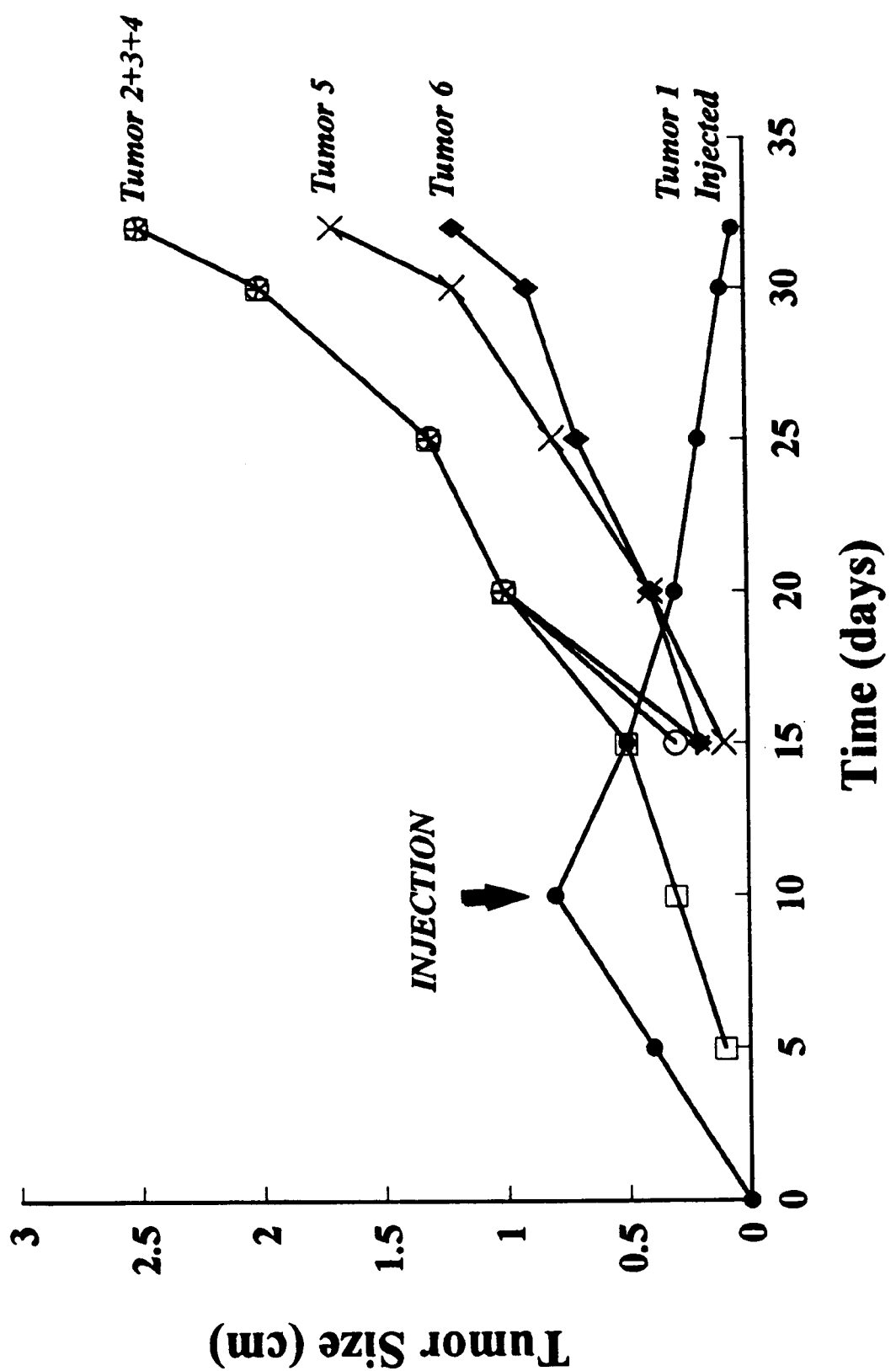
FIG. 5A is a graphical representation of pharmacological test studies of radiopharmaceuticals according to an embodiment of the present invention.

Biological efficacy test procedures for the composition of Example 1 are depicted graphically in FIG. 5A. This graph demonstrates dramatically that the growth of a tumor (Tumor 1) was arrested upon the injection of the composition of Example 1, and that the size of the treated tumor diminished until it had substantially disappeared. In comparison, five control tumors (Tumors 2 to 6), which received no treatment, grew steadily throughout the tests.

B. Biological Efficacy of Compositions of the Prior Art

Figure 5B:
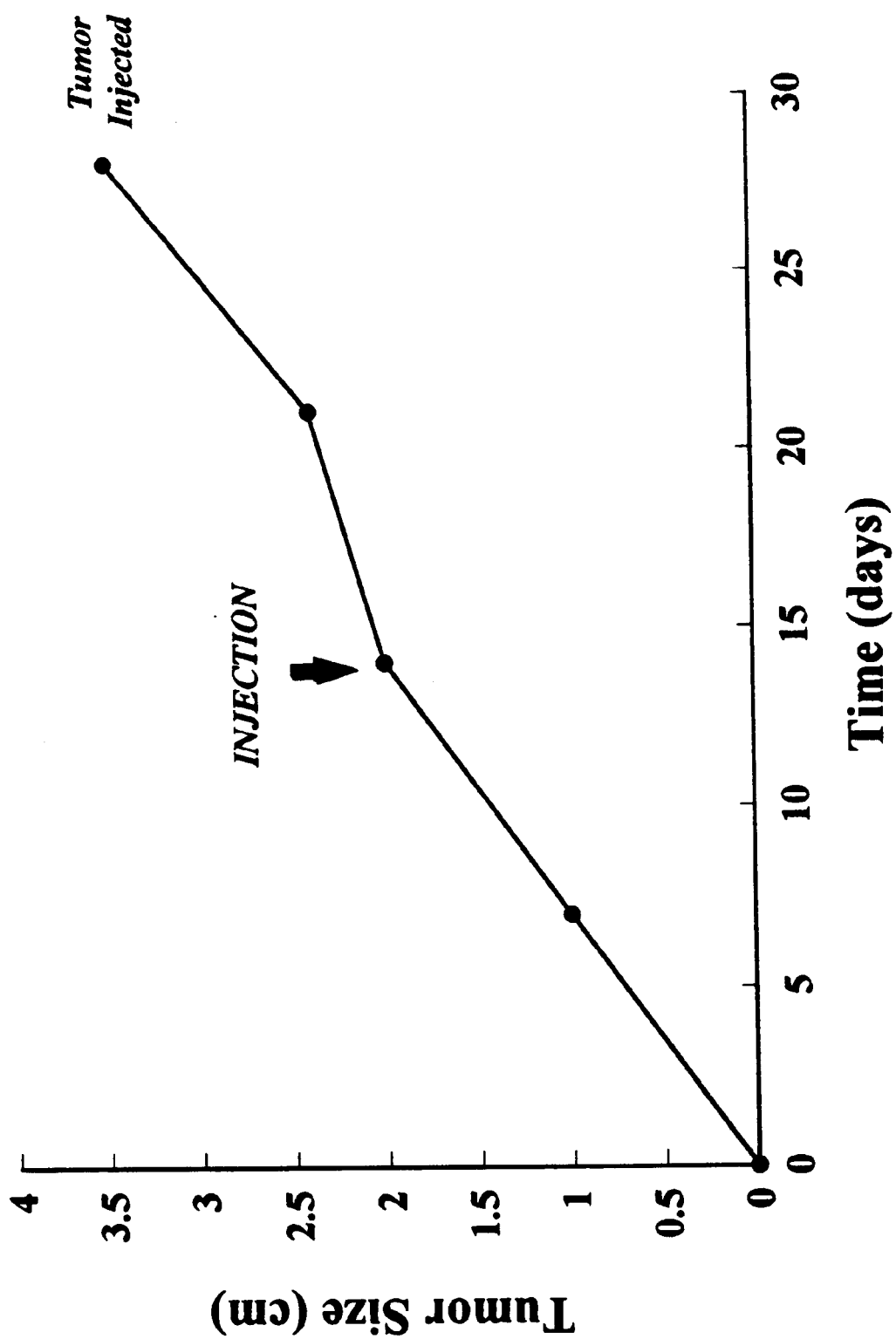
FIGS. 5B, 5C and 5D are graphical representations of pharmacological test studies of radioactive materials according to the prior art.
Figure 5C:
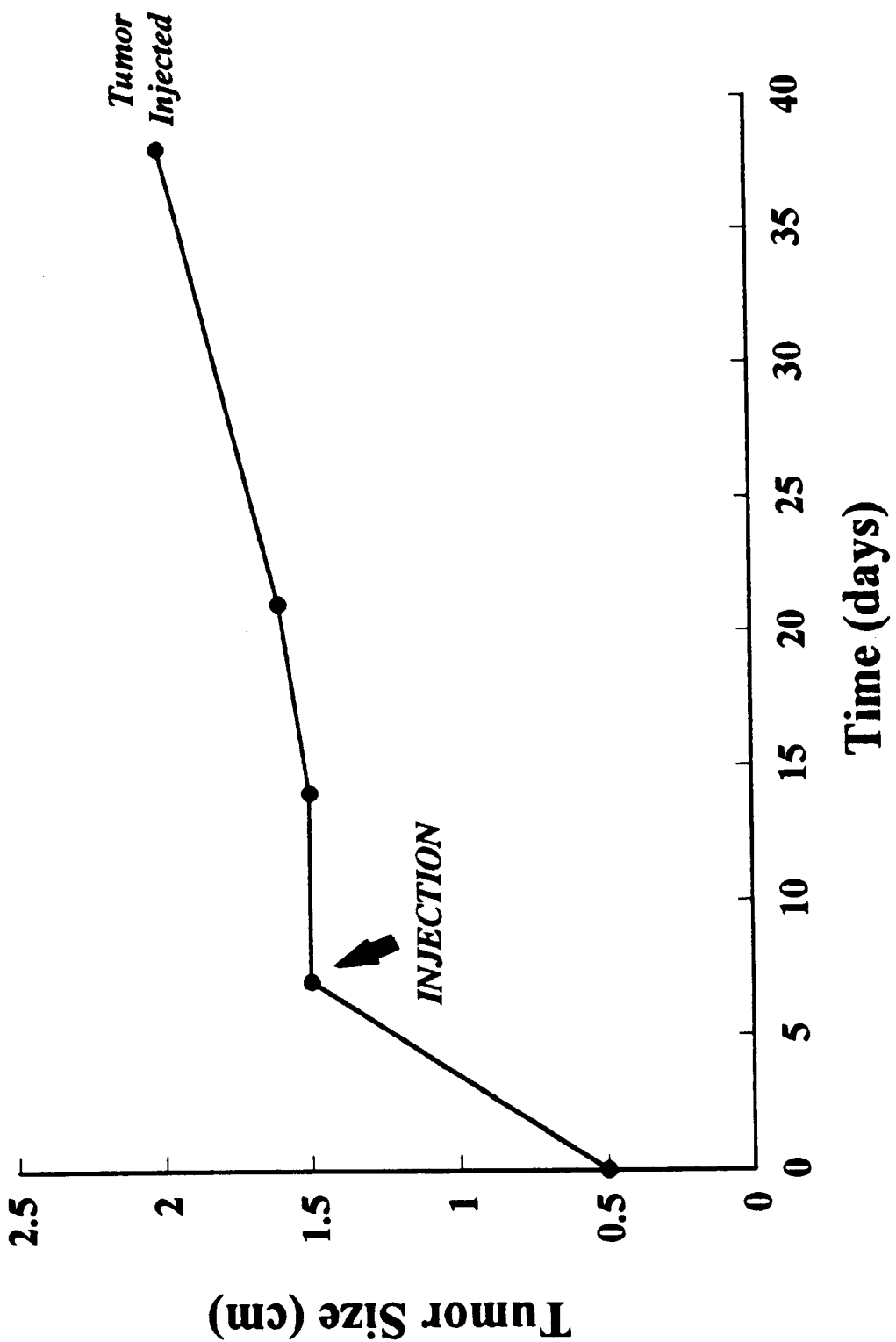
Figure 5D:
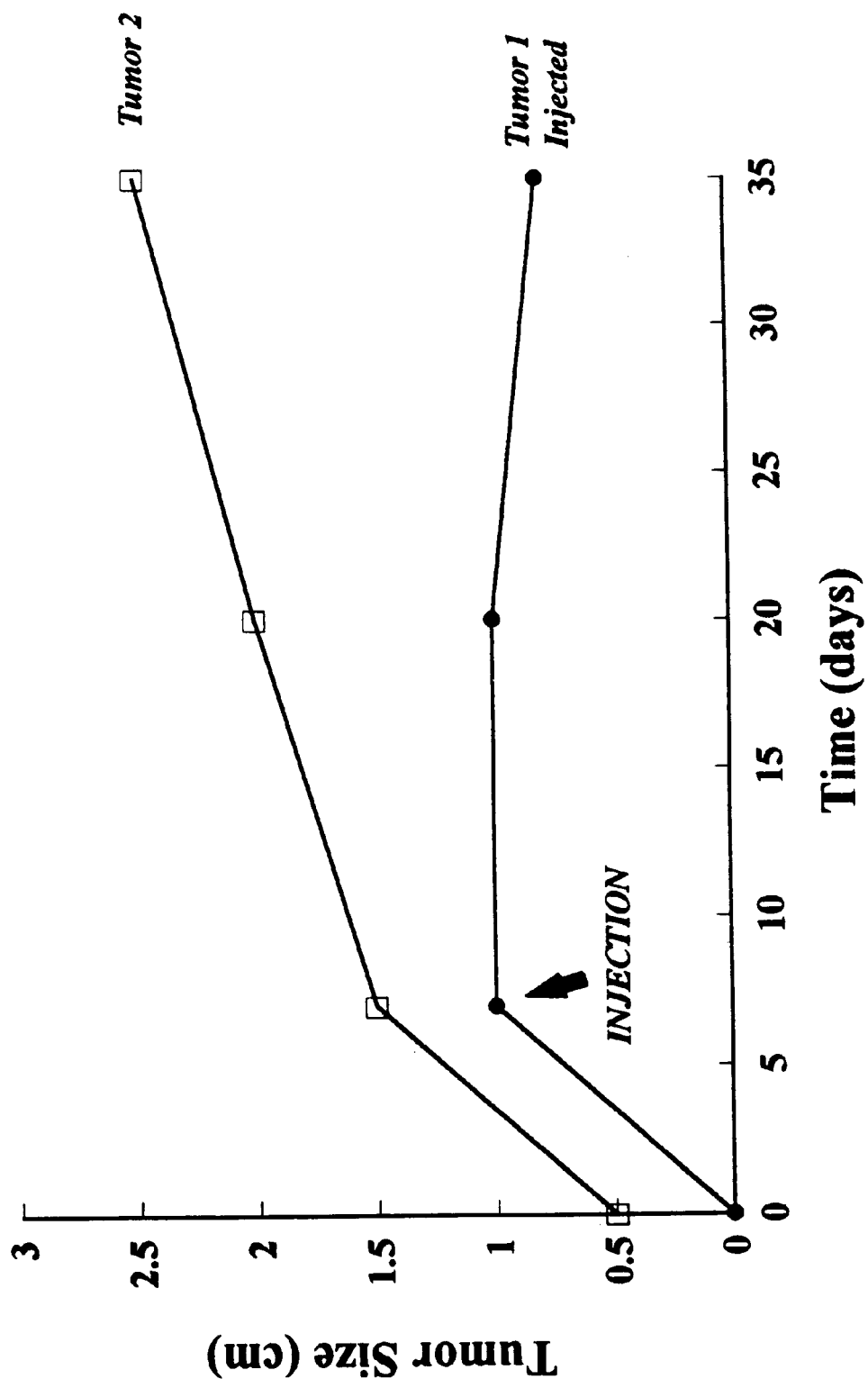

Biological efficacy test procedures for the compositions of Examples 4(A), 4(B) and 4(C) were conducted and are depicted graphically in FIGS. 5B, 5C and 5D, respectively. The tests involving the composition of Example 4(C) also included a control tumor.

Inspection of FIG. 5B reveals that the composition of Example 4(A) failed to influence tumor growth. Inspection of FIG. 5C reveals that the composition of Example 4(B) caused a brief stabilization in tumor growth upon injection. However, the tumor resumed its growth and continued to increase in size after several days. Inspection of FIG. 5D reveals that the composition of Example 4(C) caused an arrest in tumor growth. However, unlike tumors treated with the compositions of the present invention, the size of the tumor treated with the composition of Example 4(C) remained about the same. As can be seen in FIG. 5D, the size of the control tumor increased steadily.

(Gleason Grade 2). In this latter case, the radiopharmaceutical composition was also radiolabeled with $^{111}$In to permit external visualization with a gamma-camera. Complete absence of diffusion of the radiopharmaceutical composition was observed.

In all of the patients involved in this study, no immediate or late onset of undesirable side effects was observed. None of the patients experienced impairment of sexual function or vesical voiding, and none of the patients exhibited cystitis or rectal inflammation. In addition, none of the patients exhibited any symptoms associated with radiation sickness. The patients were monitored after implantation of the radiopharmaceutical composition using echography and evaluation of PSA levels. A majority of the patients received a single implant of the radioactive composition. Patients who exhibited neoplasic cellular activity, in the first control after the implant, received additional doses of the radiopharmaceutical composition with little or no side effects. The results of these pharmacological test results are set forth in the following Table 7 and are depicted graphically in FIG. 6.

TABLE 7

| PATIENT | AGE | PRE TREATMENT | | POST TREATMENT | | | | | | | |
|---|---|---|---|---|---|---|---|---|---|---|---|
| | | DATE | PSA | DATE | PSA | DATE | PSA | DATE | PSA | DATE | PSA |
| A | 61 | 12/90 | 26 | 5/92 | 4.3 | 8/93 | 1.5 | 5/94 | 1.5 | 8/94 | 1.1 |
| B | 56 | 2/91 | 1 | 6/91 | 1.5 | 6/92 | 0.5 | 3/93 | 0.5 | 11/93 | 1.6 |
| C | 73 | 7/91 | 30 | 9/91 | 20 | 6/93 | 1.4 | 12/93 | 0.8 | 4/94 | 0.4 |
| D | 73 | 9/91 | 4 | 6/92 | 1.4 | 12/92 | 1 | 6/93 | 1.5 | 12/93 | 1 |
| E | 56 | 9/91 | 45 | 11/92 | 4 | — | — | — | — | — | — |
| F | 67 | 4/92 | 24 | 9/92 | 14 | 10/92 | 14 | 4/93 | 11 | 5/93 | 12 |
| G | 67 | 4/92 | 24 | 4/93 | 11 | 7/93 | 10 | 9/93 | 10 | 1/94 | 8 |
| H | 61 | 9/92 | 24 | 4/93 | 8.2 | 10/93 | 4.4 | 3/94 | 5.2 | 7/94 | 4.4 |
| I | 60 | 6/93 | 34 | 12/93 | 30 | 3/94 | 25 | 5/94 | 17 | 10/94 | 15 |
| J | 51 | 5/94 | 62 | 10/94 | 9.6 | — | — | — | — | — | — |

| PATIENT | POST TREATMENT | | | | | | | | | |
|---|---|---|---|---|---|---|---|---|---|---|
| | DATE | PSA | DATE | PSA | DATE | PSA | DATE | PSA | DATE | PSA |
| A | — | — | — | — | — | — | — | — | — | — |
| B | 3/94 | 0.7 | 8/94 | 0.7 | — | — | — | — | — | — |
| C | 7/94 | 0.8 | 9/94 | 0.6 | — | — | — | — | — | — |
| D | 6/94 | 1 | — | — | — | — | — | — | — | — |
| E | — | — | — | — | — | — | — | — | — | — |
| F | 10/93 | 14 | 5/94 | 13 | 7/94 | 27 | 8/94 | 18 | 10/94 | 14 |
| G | 4/94 | 9 | 6/94 | 9 | — | — | — | — | — | — |
| H | — | — | — | — | — | — | — | — | — | — |
| I | — | — | — | — | — | — | — | — | — | — |
| J | — | — | — | — | — | — | — | — | — | — |

Inspection of the above table and FIG. 6 reveals that all of the patients exhibited a substantial reduction in levels of PSA, indicating a reduction in the size of the prostatic tumors.

EXAMPLE 10

This example includes a description of in vivo pharmacological test procedures in humans with radiopharmaceutical compositions within the scope of the present invention.

Radiopharmaceutical compositions of the type prepared in Example 1 were implanted in the prostates of ten patients (Patients A to J) with prostate adenocarcinomas. This involved transperineal implantation with transrectal ultrasound needle guidance. In one patient, the implantation was performed directly into the whole remaining prostatic tissue after transurethral resection of a prostatic adenoma, which showed histological evidence of prostatic adenocarcinoma

EXAMPLE 11

This example describes the preparation of a radiopharmaceutical matrix within the scope of the present invention.

A. Radiolabeling of Epoxy Resin

Steps A and B of Example 1 were repeated to provide the radiolabeled charcoal. This radiolabeled charcoal (70 mg) was combined with Araldite GY 507 Epoxy Resin (1 g) and Hardener HY 951 (1 g), and the resulting mixture was blended until homogeneous.

B. Inclusion Into Plastic Sleeve

The mixture prepared in Step A was pumped into a Dacron® sleeve having an external diameter of 1 mm, an internal diameter of 0.8 mm and a length of 1 cm. The filled Dacron® sleeve was heated to about 50° C. for about 2 to 3 hours to cure the radiolabeled epoxy resin.

EXAMPLE 12

This example includes a description of chemical and physical analysis which were conducted on the radiopharmaceutical matrix prepared in Example 11.

A. Stability Analysis

The matrix prepared in Example 11 was analyzed for possible washout of radioactivity. This analysis was conducted by storing the matrix in a glass vial containing 2 mL of distilled water. The vial was sealed, crimped and autoclaved at 1 atm for 30 min. Two samples of the distilled water supernatant (1 mL each) were analyzed for radioactivity using a radioactivity detector. The measured activity of the samples was 0.04% and 0.06%, respectively, indicating that the matrix possessed high stability.

EXAMPLE 13

This example describes experimental protocols involved in certain of the in vivo radiopharmacological test procedures.

A. Inducement of Cancers

Cancers were induced employing the methods described in Example 5A above.

B. Administration of the Matrix

The matrix prepared in Example 11 (1 cm in length with a radioactivity of approximately 300 $\mu$Ci) was injected into mammary adenocarcinomas, the liver and the muscle of the right rear leg of rats. At the conclusion of the experiments, the rats with tumors as well as the healthy rats were sacrificed. The organs, bones, treated tumors, injected livers and injected rear paws, in either case, were removed, disrupted and mineralized with sulfochromic mixture. The radioactivity of the collected urine, feces, organs, bones, injected organs and $^{32}$P standard were measured in a monochannel gamma spectrometer with an ordinary well crystal of NaI(Tl) measuring 2"×2" and using the Bremsstrahlung photons of $^{32}$P The counter was calibrated previously and the geometry of all of the measurements was maintained constant. The efficiency of the measurements was about 0.1%.

Unless indicated otherwise, the rats were kept in stainless steel metabolic cages which permitted the collection and separation of feces and urine during the in vivo experiments. Food and water were available to the rats at all times.

In the following examples, the radioactivity of the collected urine and feces was analyzed and is expressed as the "Eliminated Activity". The term "Eliminated Activity" is expressed as a percentage of the amount of radioactivity in the urine and feces, relative to the total amount of radioactivity injected into the experimental animal.

EXAMPLE 14

Figure 7A:
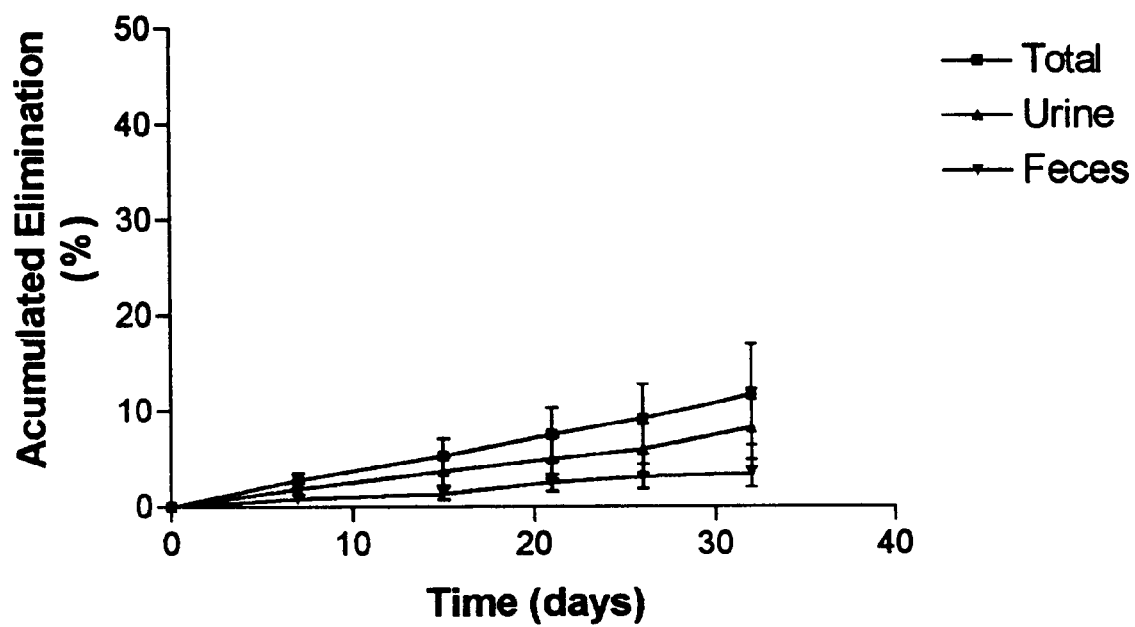
FIGS. 7A, 7B and 7C are graphical representations of studies of the biological elimination of radiopharmaceutical matrices according to an embodiment of the present invention.
Figure 7B:
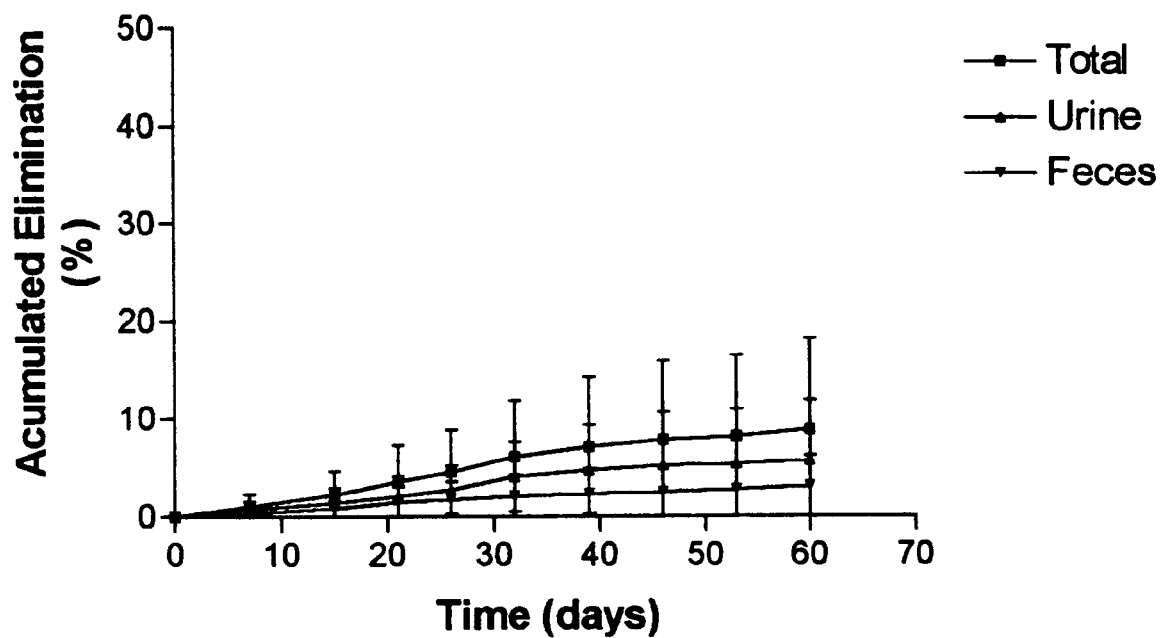
Figure 7C:
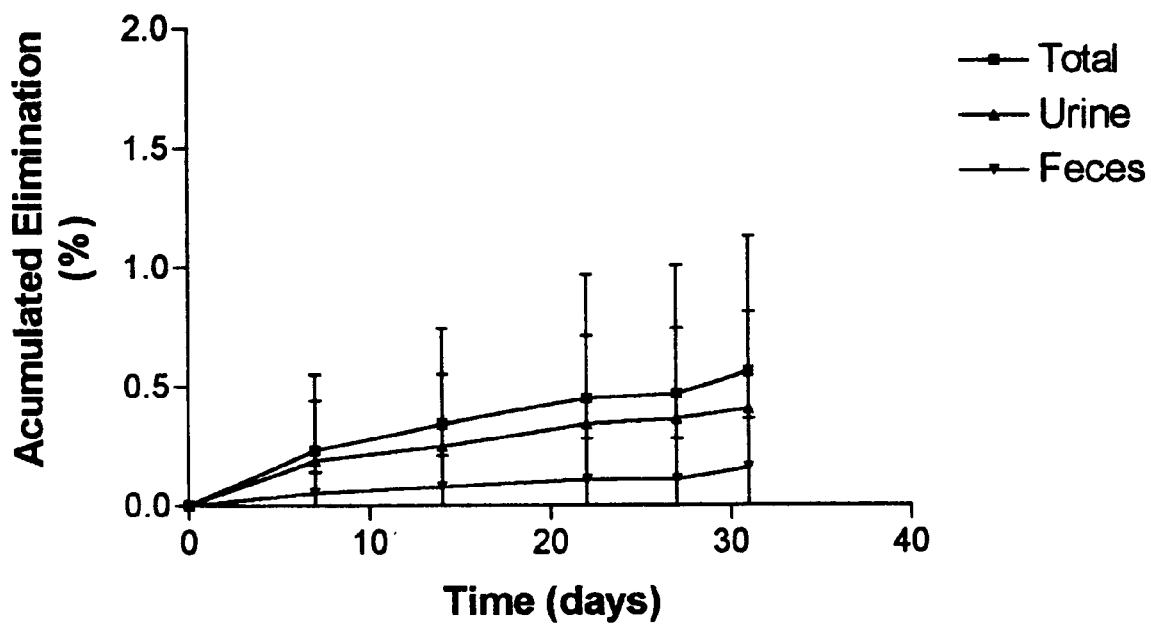

This example includes a description of biological elimination test procedures involving a radiopharmaceutical matrix of the present invention. Biological tests were conducted and involved the intratumoral administration of the matrix of Example 11 to 4 rats, referred to hereinafter as "Test 14A", the intrahepatic administration of the matrix to 3 rats ("Test 14B"), and the intramuscular administration of the matrix to 10 rats ("Test 14C"). The results of these tests are set forth in the following Table 8 and are depicted graphically in FIGS. 7A, 7B and 7C.

TABLE 8

| Test | Time (days) | Number of Animals | Eliminated Activity (%) | | |
|---|---|---|---|---|---|
| | | | Urine | Feces | Total |
| 14A | 32 | 4 | 8.22 ± 4.09 | 3.49 ± 1.47 | 11.71 ± 5.27 |
| 14B | 32 | 3 | 4.11 ± 3.58 | 2.13 ± 2.20 | 6.24 ± 5.74 |
| 14C | 31 | 10 | 0.40 ± 0.41 | 0.16 ± 0.20 | 0.56 ± 0.57 |

Test Samples 14(A), 14(B) and 14(C), and the corresponding figures (FIGS. 7A, 7B and 7C, respectively) show the eliminated activity for 4, 3 and 10 of the treated animals, respectively, as mean±standard deviation. Inspection of Table 8 above and FIGS. 7A to 7C reveals that a substantially small amount of the radioactivity administered using matrices of the present invention was eliminated from the body. In each of tests 14(A), 14(B) and 14(C), the activity in the collected urine was higher than that in the collected feces.

EXAMPLE 15

Figure 8A:
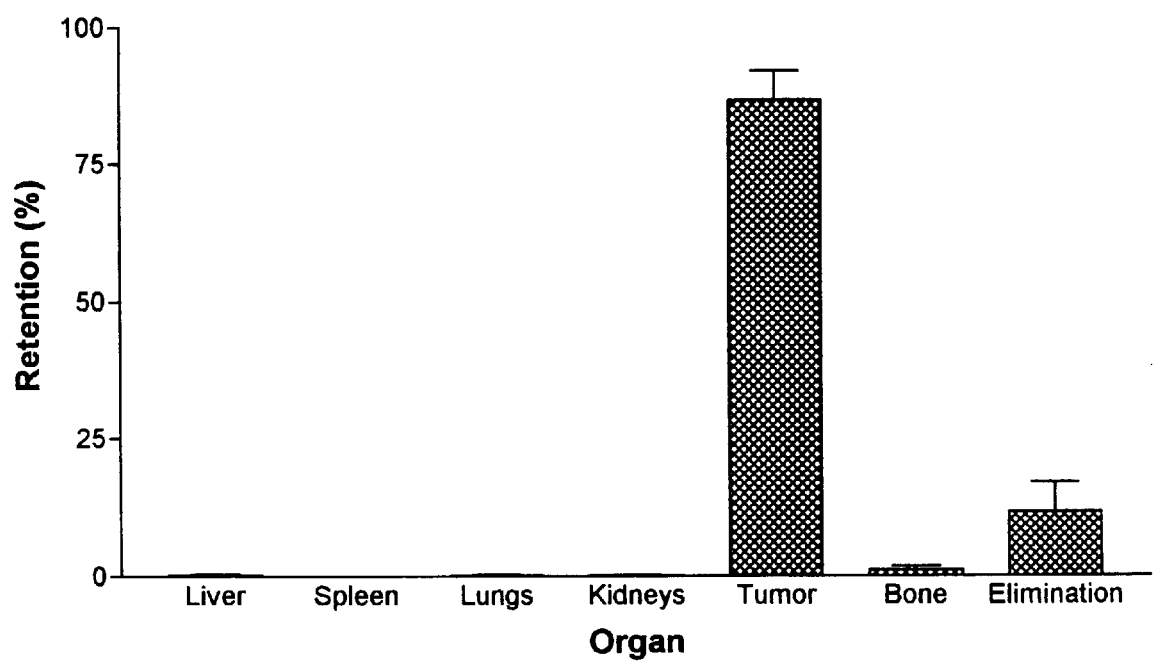
FIGS. 8A, 8B and 8C are graphical representations of pharmacological test studies of radiopharmaceutical matrices according to an embodiment of the present invention.
Figure 8B:
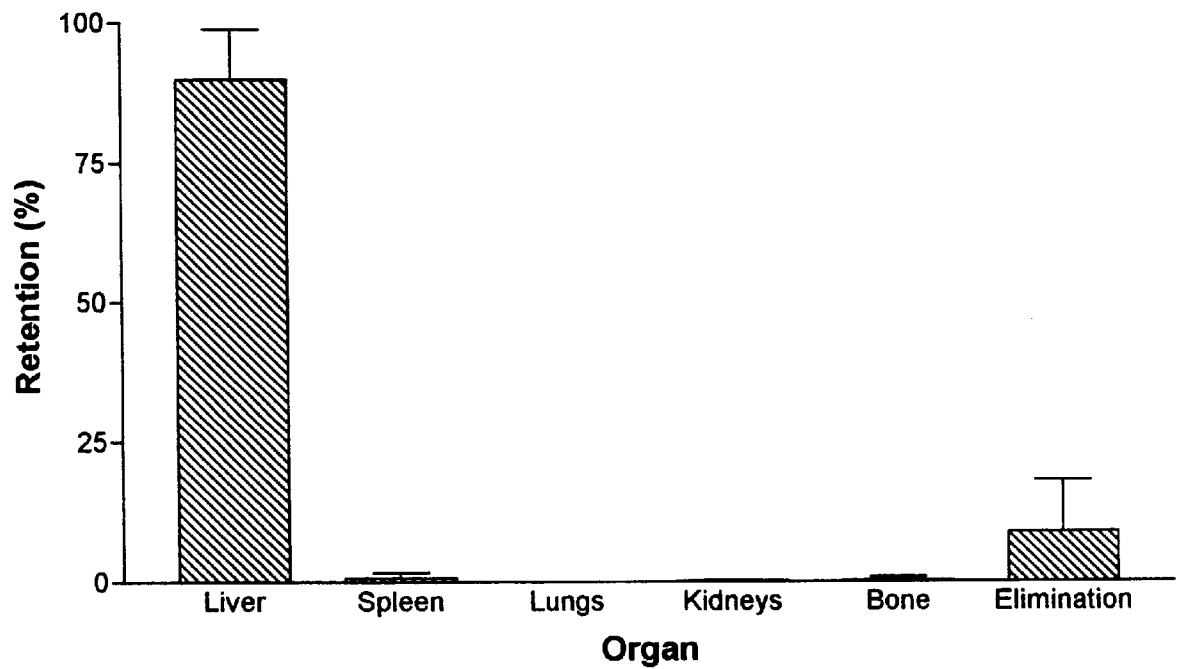
Figure 8C:
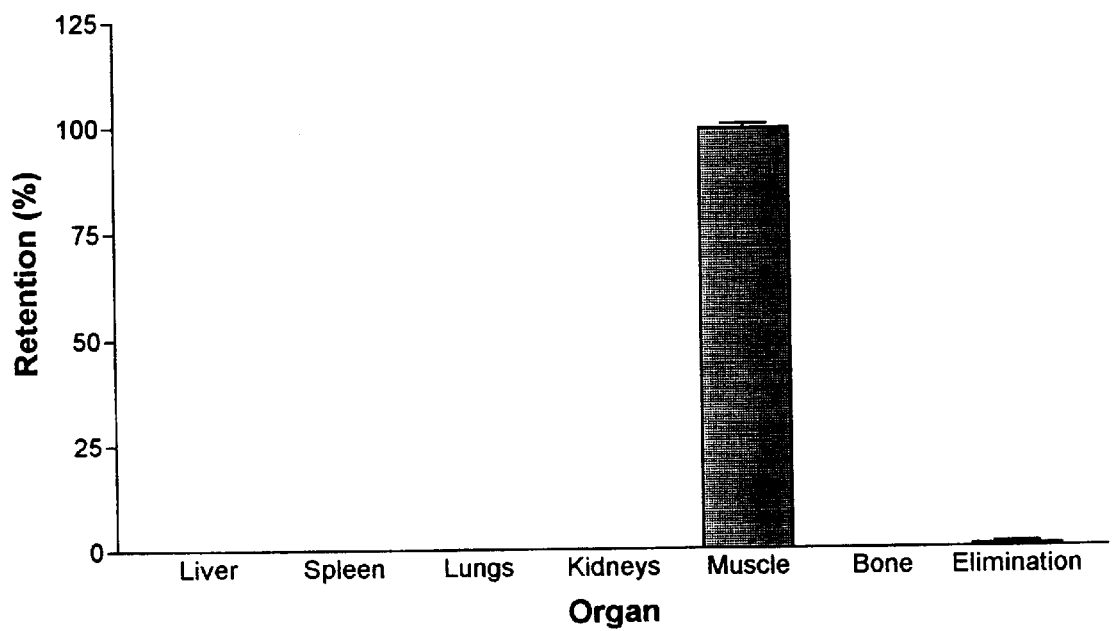

This example includes a study of the biological distribution of radioactivity after intratumoral (15A), intrahepatic (15B) and intramuscular (15C) administration of the matrix of the present invention. The study involved an analysis of the biological distribution of radioactivity in the injected organs, tissues and/or tumors, as well as in other tissues or organs in the experimental animal, particularly the bone, liver, spleen, kidneys and lungs. The biological distribution test procedures described in this example are set forth below in Table 9 and are depicted graphically in FIGS. 8A, 8B and 8C, respectively.

The numerical values in Table 9 represent percentage of radioactivity in the involved tissue, based on the total amount of administered radioactivity. The balance of the percentage of the total radioactivity measured generally corresponded to eliminated activity.

TABLE 9

| Test | Number of Animals | Injected Activity Per Organ (%) | | | | | | |
|---|---|---|---|---|---|---|---|---|
| | | Tumor | Muscle | Bone | Liver | Spleen | Kidney | Lung |
| 15A | 4 | 86.80 ± 5.45 | — | 1.05 ± 0.71 | 0.23 ± 0.21 | 0.00 ± 0.00 | 0.08 ± 0.11 | 0.14 ± 0.23 |
| 15B | 3 | — | — | 0.32 ± 0.55 | 89.86 ± 9.05 | 0.80 ± 0.92 | 0.12 ± 0.21 | 0.00 ± 0.00 |
| 15C | 10 | — | 99.42 ± 1.12 | 0.00 ± 0.00 | 0.00 ± 0.00 | 0.00 ± 0.00 | 0.00 ± 0.00 | 0.00 ± 0.00 |

Inspection of Table 9 indicates that radioactivity administered using the matrices of the present invention substantially remains in the injected tumor, organ or tissue, with negligible transport to other tissues.

The disclosures of each patent, patent application and publication cited or described in this document are hereby incorporated by reference, in their entirety.

Various modifications of the invention, in addition to those described herein, will be apparent to those skilled in the art from the foregoing description. Such modifications are also intended to fall within the scope of the appended claims.

What is claimed:

1. A radiopharmaceutical composition comprising a radioactive salt of the formula $$M^{z+}H_xP_2O_7$$

wherein:
  M is a metal ion;
  x is an integer from 0 to 3;
  z is an integer from 1 to 4;
with the proviso that the sum of x and z is equal to 4, and P comprises a radioisotope;
and a pharmaceutically acceptable carrier.

2. A radiopharmaceutical composition according to claim 1 wherein M is selected from the group consisting of indium, calcium, strontium and transition metals.

3. A radiopharmaceutical composition according to claim 2 wherein M comprises a transition metal.

4. A radiopharmaceutical composition according to claim 3 wherein said transition metal is selected from the group consisting of chromium, yttrium, holmium, samarium, iron, gold, silver, cerium and mixtures thereof.

5. A radiopharmaceutical composition according to claim 4 wherein said transition metal is selected from the group consisting of chromium and yttrium.

6. A radiopharmaceutical composition according to claim 5 wherein M comprises chromium.

7. A radiopharmaceutical composition according to claim 6 wherein x is 0 or 1 and z is 3 or 4.

8. A radiopharmaceutical composition according to claim 1 wherein said radioisotope comprises $^{32}P$.

9. A radiopharmaceutical composition according to claim 1 which is in the form of a suspension.

10. A radiopharmaceutical composition according to claim 1 wherein said radioactive salt comprises a radioisotope which emits $\beta^{31}$ particles.

11. A radiopharmaceutical composition according to claim 10 wherein said radioisotope substantially emits $\beta^-$ particles only.

12. A radiopharmaceutical composition according to claim 1 further comprising an inert support material.

13. A radiopharmaceutical composition according to claim 12 wherein said inert support material is selected from the group consisting of an adsorbent solid material and an absorbent solid material.

14. A radiopharmaceutical composition according to claim 13 wherein said inert solid material comprises a particulate support material.

15. A radiopharmaceutical composition according to claim 14 wherein said particulate support material comprises finely divided particles of carbon.

16. A radiopharmaceutical composition according to claim 1 wherein said pharmaceutically acceptable carrier is selected from the group consisting of water, buffer and saline.

17. A radiopharmaceutical composition according to claim 16 wherein said pharmaceutically acceptable carrier further comprises a thickening agent.

18. A radiopharmaceutical composition according to claim 17 wherein said thickening agent is selected from the group consisting of gelatins, polyvinylpyrrolidone and polyoxyethylene-polyoxypropylene glycol block copolymers.

19. A radiopharmaceutical composition comprising a radioactive salt of the formula $$M^{z+}H_xP_2O_7$$

wherein:
  M is a metal ion;
  x is an integer from 0 to 3; and
  z is an integer from 1 to 4;
with the provisos that the sum of x and z is equal to 4, and at least one of M, H, P or O comprises a radioisotope; and one or more polymeric resins.

20. A radiopharmaceutical composition according to claim 19 wherein said polymeric resins are selected from the group consisting of acrylic, polyester and epoxy resins.

21. A radiopharmaceutical composition according to claim 20 wherein said polymeric resin is an epoxy resin.

22. A radiopharmaceutical composition according to claim 19 wherein said composition is incorporated into a biocompatible sleeve.

23. A radiopharmaceutical composition according to claim 22 wherein said sleeve is formulated from a polymer.

24. A radiopharmaceutical composition according to claim 23 wherein said polymer of said sleeve is selected from the group consisting of polyester, polytetrafluoroethylene, polyethylene and polyorganosilicon polymers.

25. A radiopharmaceutical composition according to claim 24 wherein said polymer of said sleeve is a polyester polymer.

26. A radiopharmaceutical composition according to claim 25 wherein said polyester is polyethylene terephthalate.

27. A radiopharmaceutical composition comprising a radioactive salt of pyrophosphoric acid and one or more polymeric resins.

28. A radioactive salt of the formula $$M^{z+}H_xP_2O_7$$

wherein:
  M is a metal ion;
  x is an integer from 0 to 3;
  z is an integer from 1 to 4;
with the proviso that the sum of x and z is equal to 4, and P comprises a radioisotope.

29. A radioactive salt according to claim 28 wherein M is selected from the group consisting of indium, calcium, strontium and transition metals.

30. A radioactive salt according to claim 29 wherein M comprises a transition metal.

31. A radioactive salt according to claim 30 wherein said transition metal is selected from the group consisting of chromium, yttrium, holmium, samarium, iron, gold, silver, cerium and mixtures thereof.

32. A radioactive salt according to claim 31 wherein said transition metal is selected from the group consisting of chromium and yttrium.

33. A radioactive salt according to claim 32 wherein said transition metal comprises chromium.

34. A radioactive salt according to claim 33 wherein x is 0 or 1 and z is 3 or 4.

35. A radioactive salt according to claim 28 wherein said radioisotope comprises $^{32}P$.

36. A radioactive salt according to claim 28 which is adsorbed or absorbed on an inert support material.

37. A solid radiopharmaceutical matrix comprising a biocompatible sleeve which substantially surrounds a radiopharmaceutical composition comprising a radioactive salt of pyrophosphoric acid and one or more polymeric resins.

38. A radiopharmaceutical matrix according to claim 37 wherein said sleeve is formulated from a polymer.

39. A radiopharmaceutical matrix according to claim 38 wherein said polymer of said sleeve is selected from the group consisting of polyester, polytetrafluoroethylene, polyethylene and polyorganosilicon polymers.

40. A radiopharmaceutical matrix according to claim 39 wherein said polymer of said sleeve is a polyester polymer.

41. A radiopharmaceutical matrix according to claim 40 wherein said polyester is polyethylene terephthalate.

42. A radiopharmaceutical matrix according to claim 37 wherein said polymeric resins are selected from the group consisting of acrylic, polyester and epoxy resins.

43. A radiopharmaceutical matrix according to claim 42 wherein said polymeric resin is an epoxy resin.

44. A radiopharmaceutical composition comprising a radioactive salt substantially insoluble in aqueous media of the formula $$M^{z+}H_xP_2O_7$$

wherein:
M is a metal ion;
x is an integer from 0 to 3;
z is an integer from 1 to 4;
with the proviso that the sum of x and z is equal to 4, and at least one of M, H, P or O comprises a radioisotope; and a pharmaceutically acceptable carrier.

45. A radiopharmaceutical composition according to claim 44 wherein M is selected from the group consisting of indium, calcium, strontium and transition metals.

46. A radiopharmaceutical composition according to claim 45 wherein M comprises a transition metal.

47. A radiopharmaceutical composition according to claim 46 wherein said transition metal is selected from the group consisting of chromium, yttrium, holmium, samarium, iron, gold, silver, cerium and mixtures thereof.

48. A radiopharmaceutical composition according to claim 47 wherein said transition metal is selected from the group consisting of chromium and yttrium.

49. A radiopharmaceutical composition according to claim 48 wherein M comprises chromium.

50. A radiopharmaceutical composition according to claim 49 wherein x is 0 or 1 and z is 3 or 4.

51. A radiopharmaceutical composition according to claim 44 wherein P comprises a radioisotope.

52. A method for the treatment of cancer in a patient comprising the administration to the patient of an effective amount of a composition according to claim 44.

53. A method according to claim 52 wherein said cancer is selected from the group consisting of cancers of the head, neck, endometrium, liver, breast, ovaries, cervix and prostate.

54. A method according to claim 53 wherein said cancer comprises prostate cancer.

55. A method according to claim 52 which involves brachytherapy.

56. A method for the treatment of cancer in a patient comprising the administration to the patient of an effective amount of a radiopharmaceutical matrix according to claim 37.

57. A radiopharmaceutical kit for the preparation of a radiopharmaceutical composition of claim 44.

58. A kit according to claim 57 further comprising a pharmaceutically acceptable carrier.

59. A kit according to claim 58 wherein said pharmaceutically acceptable carrier further comprises a thickening agent.

60. A kit according to claim 57 further comprising conventional radiopharmaceutical kit components.

61. A radiopharmaceutical composition according to claim 1 wherein M is chromium, z is 3, x is 1 and the radioisotope is $^{32}P$.

62. A radiopharmaceutical composition according to claim 1 wherein M is yttrium, z is 3, x is 1 and the radioisotope is $^{32}P$.

63. A radiopharmaceutical composition according to claim 1 wherein M is $^{90}$yttrium, z is 3, x is 1 and P is the radioisotope $^{32}P$.

64. A radioactive salt according to claim 28 wherein M is chromium, z is 3, x is 1 and the radioisotope is $^{32}P$.

65. A radioactive salt according to claim 28 wherein M is yttrium, z is 3, x is 1 and the radioisotope is $^{32}P$.

66. A radioactive salt according to claim 28 wherein M is $^{90}$yttrium, z is 3, x is 1 and P is the radioisotope $^{32}P$.

67. A radioactive salt substantially insoluble in aqueous media of the formula $$M^{z+}H_xP_2O_7$$

wherein:
M is a metal ion;
x is an integer from 0 to 3;
z is an integer from 1 to 4;
with the proviso that the sum of x and z is equal to 4, at least one of M, H, P or O comprises a radioisotope, and wherein M is selected from the group consisting of indium, strontium and transition metals.

68. A radioactive salt substantially insoluble in aqueous media of the formula $$M^{z+}H_xP_2O_7$$

wherein:
M is a metal ion;
x is an integer from 0 to 3;
z is an integer from 1 to 4;
with the proviso that the sum of x and z is equal to 4, at least one of M, H, P or O comprises a radioisotope, and wherein M comprises a transition metal.

69. A radioactive salt according to claim 68 wherein said transition metal is selected from the group consisting of chromium, yttrium, holmium, samarium, iron, gold, silver, cerium and mixtures thereof.

70. A radioactive salt according to claim 69 wherein said transition metal is selected from the group consisting of chromium and yttrium.

71. A radioactive salt according to claim 70 wherein M comprises chromium.

72. A radioactive salt according to claim 71 wherein x is 0 or 1 and z is 3 or 4.

73. A radiopharmaceutical composition according to claim 44, wherein at least one of M, P or O comprises a radioisotope.

74. A radiopharmaceutical composition according to claim 73, wherein at least one of M or P comprises a radioisotope.

75. A radiopharmaceutical composition according to claim 74, wherein P comprises a radioisotope.

76. A radiopharmaceutical composition comprising a radioactive salt according to claim 44 wherein at least one of M, P or O comprises a radioisotope.

77. A radiopharmaceutical composition comprising a radioactive salt according to claim 76, wherein at least one of M or P comprises a radioisotope.

78. A radiopharmaceutical composition comprising a radioactive salt according to claim 77 wherein P comprises a radioisotope.

* * * * *